(12) United States Patent
Barvian et al.

(10) Patent No.: US 6,995,151 B2
(45) Date of Patent: Feb. 7, 2006

(54) ISOPHTHALIC ACID DERIVATIVES AS MATRIX METALLOPROTEINASE INHIBITORS

(75) Inventors: Nicole Chantel Barvian, Ann Arbor, MI (US); David Thomas Connor, Ann Arbor, MI (US); Richard Dennis Dyer, Ann Arbor, MI (US); Adam Richard Johnson, Ann Arbor, MI (US); William Chester Patt, Chelsea, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 358 days.

(21) Appl. No.: 10/075,918

(22) Filed: Feb. 13, 2002

(65) Prior Publication Data

US 2002/0156061 A1 Oct. 24, 2002

Related U.S. Application Data

(60) Provisional application No. 60/268,736, filed on Feb. 14, 2001.

(51) Int. Cl.
*A61K 31/541* (2006.01)
*A61K 31/5377* (2006.01)
*A61K 31/496* (2006.01)
*A61K 31/4545* (2006.01)
*A61K 31/4025* (2006.01)

(52) U.S. Cl. .............. 514/183; 514/210.18; 514/227.8; 514/231.8; 514/252.11; 514/316; 514/422; 544/60; 544/78; 544/357; 546/189; 548/518; 548/950; 548/962

(58) Field of Classification Search ................ 548/962, 548/950, 518; 546/189; 544/357, 60, 78; 514/316, 422, 252.11, 231.8, 227.8, 210.18, 514/183
See application file for complete search history.

(56) References Cited

U.S. PATENT DOCUMENTS

| | | | |
|---|---|---|---|
| 5,130,317 A | 7/1992 | Baader et al. | |
| 5,260,323 A | 11/1993 | Baader et al. | |
| 5,519,038 A | 5/1996 | Baader et al. | |
| 5,948,780 A | 9/1999 | Peterson, Jr. et al. | |
| 6,008,243 A | 12/1999 | Bender et al. | |
| 2003/0229103 A1 | 12/2003 | Weithmann et al. | |

FOREIGN PATENT DOCUMENTS

| | | |
|---|---|---|
| CA | 2082076 | 5/1993 |
| EP | 0418797 | 3/1991 |
| EP | 0463592 | 1/1992 |
| EP | 0935963 | 8/1999 |
| EP | 1138680 | 10/2001 |
| JP | 5193260 | 8/1993 |
| WO | WO9905148 | 2/1999 |
| WO | 0009485 | 2/2000 |
| WO | WO0105389 | 1/2001 |
| WO | 0112611 | 2/2001 |
| WO | WO 01/63244 A1 | 8/2001 |
| WO | 0234726 | 5/2002 |
| WO | 0234753 | 5/2002 |
| WO | 02064368 | 8/2002 |
| WO | 02064371 | 8/2002 |
| WO | 03049738 | 6/2003 |

OTHER PUBLICATIONS

Chen JM et al., "Structure-Based Design of a Novel, Potent, and Selective Inhibitor for MMP-13 Utilizing NMR Spectroscopy and Computer-Aided Molecular Design", Journal of the American Chemical Society 2000; 122:9648-9654.
Boger, DL et al., Identification of a novel class of small-molecule antiangiogenic agents through the screening of combinatorial libraries which function by inhibiting the binding and localization of proteinase MMP2 to integrin. alpha.V. beta. 3, Journal of the American Chemical Society 2001; 123:1280-1288.

(Continued)

*Primary Examiner*—Cecilia J. Tsang
*Assistant Examiner*—Taylor Victor Oh
(74) *Attorney, Agent, or Firm*—Claude F. Purchase, Jr.; Charles W. Ashbrook; Todd M. Crissey

(57) ABSTRACT

Selective MMP-13 inhibitors are isophthalic acid derivatives of the formula

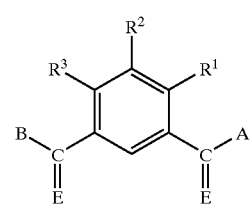

wherein:
$R^1$, $R^2$, and $R^3$ independently are hydrogen, halo, hydroxy, $C_1$–$C_6$ alkyl, $C_1$–$C_6$ alkoxy, $C_2$–$C_6$ alkenyl, $C_2$–$C_6$ alkynyl, $NO_2$, $NR^4R^5$, CN, or $CF_3$;
E is independently O or S;
A and B independently are $OR^4$ or $NR^4R^5$;
each $R^4$ and $R^5$ independently are H, $C_1$–$C_6$ alkyl, $C_2$–$C_6$ alkenyl, $C_2$–$C_6$ alkynyl, $(CH_2)_n$ aryl, $(CH_2)_n$ cycloalkyl, $(CH_2)_n$ heteroaryl, or $R^4$ and $R^5$ when taken together with the nitrogen to which they are attached complete a 3- to 8-membered ring, optionally containing a heteroatom selected from O, S, or NH, and optionally substituted or unsubstituted;
n is 0 to 6;
or a pharmaceutically acceptable salt thereof. The compounds are useful for treating diseases in a mammal that are mediated by MMP enzymes.

8 Claims, No Drawings

OTHER PUBLICATIONS

Silletti, S. et al, "Disruption of matrix metalloproteinase 2 binding to integrin alpha. v. beta. 3 by an organic molecule inhibits angiogenesis and tumor growth in vivo", Proceeding of the National Academy of Sciences of the United States of America 2001; 98(1)119-124.

Milton J. et al, "Biaryl acids: novel non-nucleoside inhibitors of HIV reverse transcriptase types 1 and 2", Bioorganic & Medicinal Chemistry Letters, Oxford, GB 1998; 8:2623-2628.

Montana, John et al, "The design of selective non-substrate-based matrix metalloproteinase inhibitors", Current Opinion in Drug Discovery & Development, 2000; 3(4), pp 353-361.

Clark, Ian, et al, "Matrix metalloproteinase inhibitors in the treatment of arthritis", Current Opinions in Anti-inflammatory & Immunomodulatory Investigational Drugs, 2000; 2(1), pp 16-25.

Chen, James, et al, "Structure-Based Design of a Novel, Potent, and Selective Inhibitor for MMP-13 Utilizing NMR Spectroscopy and Computer-Aided Molecular Design", J. Am. Chem. Soc., 2000, 122; pp 9648-9654.

International Search Report for PCT/IB02/00344, which corresponds to US10/075,918.

Office Action mailed Jun. 16, 2003 in U.S. Appl. No. 10/264,764.

Ye, et al., "Catalytic Domains of Matrix Metalloproteinases: A Molecular Biology Approach to Drug Discovery", Curr. Med.Chem., 1996; 3:407-418.

LoveJoy, et al., "Crystal structures of MMP-1 and -13 reveal the structural basis for selectivity of collagenase inhibitors", Nature Structural Biol., 1999; 6:217-221.

Moy, et al., High-resolution solution structure of the catalytic fragment of human collagenase-3 (MMP-13) complexed with a hydroxamic acid inhibitor , J. Mol. Biol., 2000; 302:671-689.

Mitchell, et al., "Cloning, Expression, and Type II Collagenolytic Activity of Matrix Metalloproteinase-13 from Human Osteoarthritic Cartilage", J. Clin. Invest., 1996; 97(3):761-768.

Neuhold, et al., "Postnatal expression in hyaline cartilage of constitutively active human collagenase-3 (MMP-13) induces osteoarthritis in mice", J. Clin. Invest., 2001; 107: 35-44.

Dahlberg, et al., Selective Enhancement of Collagenase-Mediated Cleavage of Resident Type II Collagen in Cultured Osteoarthritic Cartilage and Arrest with a Synthetic Inhibitor that Spares Collagenase I (Matrix Metalloproteinase 1), Arthrit. & Rheum., 2000; 43(3): 673-682.

Billinghurst, et al., "Comparison of the Degradation of Type II Collagen and Proteoglycan in Nasal and Articular Cartilages Induced by Interleuken-1 and the Selective Inhibition of Type II Collagen Cleavage by Collagenase", Arthrit. & Rheum., 2000; 43(3):664-672.

Billinghurst, et al., "Enhanced Cleavage of Type II Collagen by Collagenases in Osteoarthritic Articular Cartilage", J. Clin. Invest., 1997; 99:1534-1545.

Hirota, et al., "Novel Synthesis of Pyrido[3,4-d]pyrimidines, Pyrido[2,3-d]-pyrimidines, and Quinazolines via Palladium-Catalyzed Oxidative coupling", Heterocycles, 1994; 37(1): 563-570.

ISOPHTHALIC ACID DERIVATIVES AS MATRIX METALLOPROTEINASE INHIBITORS

CROSS-REFERENCE TO RELATED APPLICATIONS

This application claims benefit of priority from U.S. provisional application No. 60/268,736, filed Feb. 14, 2001.

FIELD OF THE INVENTION

This invention relates to isophthalic acid derivatives which inhibit matrix metalloproteinase enzymes and thus are useful for treating diseases resulting from tissue breakdown such as heart disease, multiple sclerosis, osteo- and rheumatoid arthritis, atherosclerosis, and osteoporosis.

BACKGROUND OF THE INVENTION

Matrix metalloproteinases (sometimes referred to as MMPs) are naturally occurring enzymes found in most mammals. Over-expression and activation of MMPs or an imbalance between MMPs and inhibitors of MMPs have been suggested as factors in the pathogenesis of diseases characterized by the breakdown of extracellular matrix or connective tissues.

Stromelysin-1 and gelatinase A are members of the matrix metalloproteinases (MMP) family. Other members include fibroblast collagenase (MMP-1), neutrophil collagenase (MMP-8), gelatinase B (92 kDa gelatinase) (MMP-9), stromelysin-2 (MMP-10), stromelysin-3 (MMP-11), matrilysin (MMP-7), collagenase 3 (MMP-13), TNF-alpha converting enzyme (TACE), and other newly discovered membrane-associated matrix metalloproteinases (Sato H., Takino T., Okada Y., Cao J., Shinagawa A., Yamamoto E., and Seiki M., *Nature,* 1994;370:61–65). These enzymes have been implicated with a number of diseases which result from breakdown of connective tissue, including such diseases as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis. A method for preventing and treating these and other diseases is now recognized to be by inhibiting matrix metalloproteinase enzymes, thereby curtailing and/or eliminating the breakdown of connective tissues that results in the disease states.

There is a catalytic zinc domain in matrix metalloproteinases that is typically the focal point for inhibitor design. The modification of substrates by introducing zinc chelating groups has generated potent inhibitors such as peptide hydroxamates and thiol-containing peptides. Peptide hydroxamates and the natural endogenous inhibitors of MMPs (TIMPs) have been used successfully to treat animal models of cancer and inflammation. MMP inhibitors have also been used to prevent and treat congestive heart failure and other cardiovascular diseases, U.S. Pat. No. 5,948,780.

A major limitation on the use of currently known MMP inhibitors is their lack of specificity for any particular enzyme. Recent data has established that specific MMP enzymes are associated with some diseases, with no effect on others. The MMPs are generally categorized based on their substrate specificity, and indeed the collagenase subfamily of MMP-1, MMP-8, and MMP-13 selectively cleave native interstitial collagens, and thus are associated only with diseases linked to such interstitial collagen tissue. This is evidenced by the recent discovery that MMP-13 alone is over expressed in breast carcinoma, while MMP-1 alone is over expressed in papillary carcinoma (see Chen et al., *J. Am. Chem. Soc.*, 2000;122:9648–9654).

There appears to be few selective inhibitors of MMP-13 reported. A compound named WAY-170523 has been reported by Chen et al., supra., 2000, and a few other compounds are reported in PCT International Publication No. WO 01/63244 A1, as allegedly selective inhibitors of MMP-13. Further, U.S. Pat. No. 6,008,243 discloses inhibitors of MMP-13. However, no selective or nonselective inhibitor of MMP-13 has been approved and marketed for the treatment of any disease in any mammal. Accordingly, the need continues to find new low molecular weight compounds that are potent and selective MMP inhibitors, and that have an acceptable therapeutic index of toxicity/potency to make them amenable for use clinically in the prevention and treatment of the associated disease states. An object of this invention is to provide a group of selective MMP-13 inhibitor compounds characterized as being isophthalic acid derivatives.

SUMMARY OF THE INVENTION

This invention provides a method for inhibiting matrix metalloproteinase enzymes, and especially MMP-13, using an isophthalic acid or analog thereof. The invention is more particularly directed to inhibiting MMP enzymes comprising administering to a mammal an MMP inhibiting amount of a compound defined by Formula I

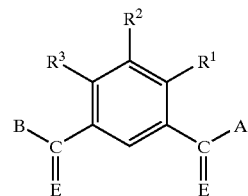

wherein $R^1$, $R^2$, and $R^3$ independently are hydrogen, halo, hydroxy, $C_1$–$C_6$ alkyl, $C_1$–$C_6$ alkoxy, $C_2$–$C_6$ alkenyl, $C_2$–$C_6$ alkynyl, $NO_2$, $NR^4R^5$, CN, or $CF_3$;

E is independently O or S;

A and B independently are $OR^4$ or $NR^4R^5$;

each $R^4$ and $R^5$ independently are H, $C_1$–$C_6$ alkyl, $C_2$–$C_6$ alkenyl, $C_2$–$C_6$ alkynyl, $(CH_2)_n$ aryl, $(CH_2)_n$ cycloalkyl, $(CH_2)_n$ heteroaryl, or $R^4$ and $R^5$ when taken together with the nitrogen to which they are attached complete a 3- to 8-membered ring, optionally containing a heteroatom selected from O, S, or NH, and optionally substituted or unsubstituted;

n is an integer from 0 to 6;

or a pharmaceutically acceptable salt thereof.

Another invention embodiment is a method of inhibiting MMP enzymes in a mammal, comprising administering to the mammal an MMP inhibiting effective amount of a compound of Formula II

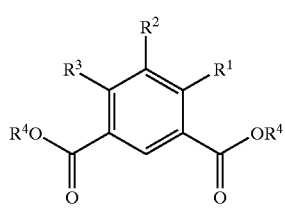

or a pharmaceutically acceptable salt thereof, wherein $R^1$, $R^2$, and $R^3$ are as defined above, and each $R^4$ independently is as defined above.

Another invention embodiment is a method of inhibiting MMP enzymes in a mammal, comprising administering to the mammal an MMP inhibiting effective amount of a compound of Formula III

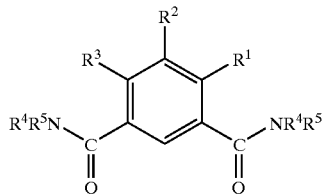

III or a pharmaceutically acceptable salt thereof,
wherein $R^1$, $R^2$, and $R^3$ are as defined above, and each $R^4$ and $R^5$ independently are as defined above.

Another invention embodiment is a method of inhibiting MMP enzymes in a mammal, comprising administering to the mammal an MMP inhibiting effective amount of a compound of Formula IV

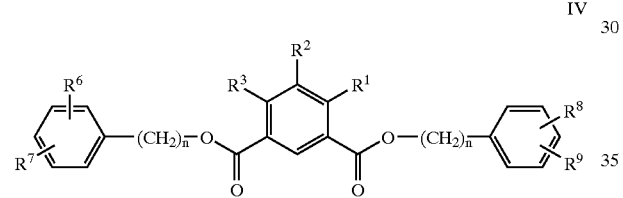

IV or a pharmaceutically acceptable salt thereof,
wherein n, $R^1$, $R^2$, and $R^3$ are as defined above, and $R^6$, $R^7$, $R^8$, and $R^9$ independently are hydrogen, halo, $C_1$–$C_6$ alkyl, $C_1$–$C_6$ alkoxy, nitro, or $NH_2$.

Another invention embodiment is a method of inhibiting MMP enzymes in a mammal, comprising administering to the mammal an MMP inhibiting effective amount of a compound of Formula V

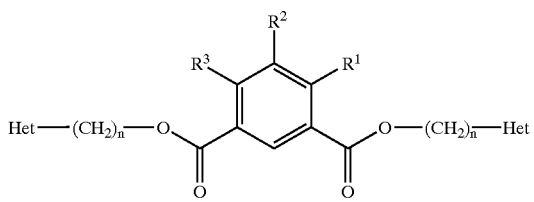

V or a pharmaceutically acceptable salt thereof,
wherein n, $R^1$, $R^2$, and $R^3$ are as defined above, and Het is an unsubstituted or substituted heteroaryl group.

Another invention embodiment is a method of inhibiting MMP enzymes in a mammal, comprising administering to the mammal an MMP inhibiting effective amount of a compound of Formula VI

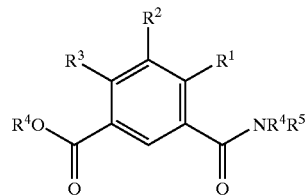

VI or a pharmaceutically acceptable salt thereof,
wherein $R^1$, $R^2$, and $R^3$ are as defined above, and each $R^4$ and $R^5$ independently are as defined above.

A further embodiment of this invention is a compound selected from:
4-Methoxy-N,N'-bis-(4-methoxybenzyl)-isophthalamide;
Isophthalic acid di-(2,1,3-benzothiadiazol-5-yl) methyl ester;
4-Methoxy-isophthalic acid dibenzyl ester;
4-Methoxy-isophthalic acid dipyridin-4-ylmethyl ester;
Isophthalic acid bis-(4-fluoro-benzyl) ester;
Isophthalic acid bis-(3-fluoro-benzyl) ester;
Isophthalic acid bis-(4-methoxy-benzyl) ester;
Isophthalic acid bis-(3-methoxy-benzyl) ester;
Isophthalic acid bis-(1,3-benzodioxol-5-ylmethyl) ester;
N,N'-Bis-(3-fluoro-benzyl)-isophthalamide;
4-Acetyl-isophthalic acid dibenzyl ester;
4-Methoxycarbonylmethoxy-isophthalic acid dibenzyl ester;
N,N'-Bis-1,3-benzodioxol-5-ylmethyl-4-methoxy-isophthalamide;
N-1,3-Benzodioxol-5-ylmethyl-4-methoxy-N'-(4-methoxy-benzyl)-isophthalamide;
4-Methoxy-N,N'-bis-(4-methoxy-benzyl)-isophthalamide;
N-1,3-Benzodioxol-5-ylmethyl-N'-(4-chloro-benzyl)-4-methoxy-isophthalamide;
N-Benzyl-4-methoxy-N'-(4-methoxy-benzyl)-isophthalamide;
N'-Benzyl-4-methoxy-N-(4-methoxy-benzyl)-isophthalamide;
4-Methoxy-N-(4-methoxy-benzyl)-N'-pyridin-4-ylmethyl-isophthalamide;
N'-1,3-Benzodioxol-5-ylmethyl-4-methoxy-N-(2-phenoxy-ethyl)-isophthalamide;
N-1,3-Benzodioxol-5-ylmethyl-4-methoxy-N'-(2-phenoxy-ethyl)-isophthalamide;
N-1,3-Benzodioxol-5-ylmethyl-N'-furan-2-ylmethyl-isophthalamide;
N'-1,3-Benzodioxol-5-ylmethyl-N-(2-ethoxy-ethyl)4-methoxy-isophthalamide;
N,N'-Bis-(3-hydroxymethyl-phenyl)-isophthalamide;
N-Benzyl-4-methoxy-N'-(2-phenoxy-ethyl)-isophthalamide;
4-Methoxy-N,N'-bis-(4-methyl-benzyl)-isophthalamide;
4-Methoxy-N,N'-bis-(3-methoxy-benzyl)-isophthalamide;
N-1,3-Benzodioxol-5-ylmethyl-4-methoxy-N'-(4-methoxy-benzyl)-isophthalamide;
N-1,3-Benzodioxol-5-ylmethyl-isophthalamic acid, (4-carboxyphenyl) methyl ester;
4-{[3-(3-Methoxy-benzylcarbamoyl)-benzoylamino]-methyl}-benzoic acid;
4-Methoxy-isophthalic acid di-2,1,3-benzothiadiazol-5-ylmethyl ester;

4-{[3-(3-Methoxy-benzylcarbamoyl)-benzoylamino]-methyl}-benzoic acid methyl ester;
N-(3-Methoxy-benzyl)-N'-(4-nitro-benzyl)-isophthalamide;
N-(3,4-Dichloro-benzyl)-N'-pyridin-4-ylmethyl-isophthalamide;
N1,N3-Bis-1,3-benzodioxol-5-ylmethyl-4-ethoxy-isophthalamide;
N-(4-Chloro-benzyl)-N'-(3-methoxy-benzyl)-isophthalamide;
N-(3,4-Dichloro-benzyl)-N'-(3-methoxy-benzyl)-isophthalamide;
N-(4-Methoxy-benzyl)-N'-(3-methoxy-benzyl)-isophthalamide;
N,N'-Bis-(4-fluoro-3-methoxy-benzyl)-isophthalamide;
4-Ethoxy-N1,N3-bis-(3-methoxy-benzyl)-isophthalamide;
N1,N3-Bis-1,3-benzodioxol-5-ylmethyl-4-ethoxy-isophthalamide;
N-(3-Methoxy-benzyl)-N'-pyridin-3-ylmethyl-isophthalamide;
N-(3-Methoxy-benzyl)-N'-pyridin-4-ylmethyl-isophthalamide;
N1-1,3-Benzodioxol-5-ylmethyl-N3-pyridin-3-ylmethyl-isophthalamide;
N-(3-Methoxy-benzyl)-N'-(3-trifluoromethoxy-benzyl)-isophthalamide;
N1,N3-Bis-1,3-benzodioxol-5-ylmethyl-4-isopropoxy-isophthalamide;
4-Isopropoxy-N1,N3-bis-(3-methoxy-benzyl)-isophthalamide;
N1-Benzyl-4-methoxy-N3-(4-methoxy-benzyl)-isophthalamide;
N1-1,3-Benzodioxol-5-ylmethyl-4-methoxy-N3-(4-methoxy-benzyl)-isophthalamide;
N1-1,3-Benzodioxol-5-ylmethyl-4-methoxy-N3-(2-phenoxy-ethyl)-isophthalamide;
N1-Benzyl-4-methoxy-N3-(2-phenoxy-ethyl)-isophthalamide;
N1-1,3-Benzodioxol-5-ylmethyl-N3-(4-chloro-benzyl)-4-methoxy-isophthalamide;
N3-1,3-Benzodioxol-5-ylmethyl-4-methoxy-N1-(4-methoxy-benzyl)-isophthalamide;
N3-Benzyl-4-methoxy-N1-(4-methoxy-benzyl)-isophthalamide;
N3-1,3-Benzodioxol-5-ylmethyl-4-methoxy-N1-(2-phenoxy-ethyl)-isophthalamide;
N3-1,3-Benzodioxol-5-ylmethyl-N1-(2-ethoxy-ethyl)4-methoxy-isophthalamide;
4-Methoxy-N1-(4-methoxy-benzyl)-N3-pyridin-4-ylmethyl-isophthalamide;
4-Amino-N1,N3-bis-1,3-benzodioxol-5-ylmethyl-isophthalamide;
4-Acetylamino-N1,N3-bis-1,3-benzodioxol-5-ylmethyl-isophthalamide;
N-(3-Methoxy-benzyl)-N'-pyridin-3-ylmethyl-isophthalamide;
N-(3-Methoxy-benzyl)-N'-pyridin4-ylmethyl-isophthalamide;
N1-1,3-Benzodioxol-5-ylmethyl-N3-pyridin-3-ylmethyl-isophthalamide;
N-(4–Chloro-benzyl)-N'-(3-methoxy-benzyl)-isophthalamide;
N-(3,4-Dichloro-benzyl)-N'-(3-methoxy-benzyl)-isophthalamide;
N-(4-Methoxy-benzyl)-N'-(3-methoxy-benzyl)-isophthalamide;
N-(3-Methoxy-benzyl)-N'-(4-methyl-benzyl)-isophthalamide;
N,N'-Bis-(4-fluoro-3-methoxy-benzyl)-isophthalamide;
({3-[(1,3-Benzodioxol-5-ylmethyl)-carbamoyl]-benzoyl}-benzyl-amino)-acetic acid;
N-Benzo[1,3]dioxol-5-ylmethyl-isophthalamic(4-hydroxymethyl-benzoic acid) ester;
N-(3,4-Dichloro-benzyl)-N'-pyridin4-ylmethyl-isophthalamide;
N-(3-Methoxy-benzyl)-N'-(4-nitro-benzyl)-isophthalamide;
4-{[3-(3-Methoxy-benzylcarbamoyl)-benzoylamino]-methyl}-benzoic acid methyl ester;
N-3-Methoxybenzyl-isophthalamic(4-hydroxymethyl-benzoic acid) ester;
4-{[3-(3-Methoxy-benzylcarbamoyl)-benzoylamino]-methyl}-benzoic acid;
N-(3-Amino-benzyl)-N'-(3-methoxy-benzyl)-isophthalamide;
N-(3-Methoxy-benzyl)-N'-(3-nitro-benzyl)-isophthalamide;
4-Ethoxy-N'1,N"3-bis-(3-methoxy-benzyl)-isophthalamide;
N1,N3-Bis-1,3-benzodioxol-5-ylmethyl-4-ethoxy-isophthalamide;
N1,N3-Bis-1,3-benzodioxol-5-ylmethyl-4-propoxy-isophthalamide;
N1,N3-Bis-1,3-benzodioxol-5-ylmethyl-4-isopropoxy-isophthalamide;
N1,N3-Bis-2,1,3-benzothiadiazol-5-ylmethyl-4-methoxy-isophthalamide; and
4-Methoxy-isophthalic acid di-2,1,3-benzothiadiazol-5-ylmethyl ester.

A further embodiment of this invention is a pharmaceutical composition, comprising a compound of Formula I, or a pharmaceutically acceptable salt thereof, admixed with a pharmaceutically acceptable carrier, excipient, or diluent.

Another invention embodiment is a pharmaceutical composition, comprising a compound of any one of Formulas II to VI, or a pharmaceutically acceptable salt thereof, admixed with a pharmaceutically acceptable carrier, excipient, or diluent.

A further embodiment of this invention is use of a compound of Formula I, or a pharmaceutically acceptable salt thereof, in the manufacture of a medicament for the treatment of a disease mediated by an MMP-13 enzyme.

Another invention embodiment is use of a compound of any one of Formulas II, III, IV, V, or VI, or a pharmaceutically acceptable salt thereof, in the manufacture of a medicament for the treatment of a disease mediated by an MMP-13 enzyme.

Another invention embodiment is use of a compound of Formula I, or a pharmaceutically acceptable salt thereof, in the manufacture of a medicament for the treatment of cancer.

Another invention embodiment is use of a compound of Formula I, or a pharmaceutically acceptable salt thereof, in the manufacture of a medicament for the treatment of rheumatoid arthritis.

Another invention embodiment is use of a compound of Formula I, or a pharmaceutically acceptable salt thereof, in the manufacture of a medicament for the treatment of osteoarthritis.

Another invention embodiment is use of a compound of Formula I, or a pharmaceutically acceptable salt thereof, in the manufacture of a medicament for the treatment of heart failure.

Another invention embodiment is use of a compound of Formula I, or a pharmaceutically acceptable salt thereof, in the manufacture of a medicament for the treatment of inflammation.

A further embodiment is a method for treating a disease mediated by an MMP-13 enzyme, comprising administering to a patient suffering from such a disease an effective amount of a compound of Formula I, or a pharmaceutically acceptable salt thereof.

Another embodiment of this invention is a method for inhibiting an MMP-13 enzyme in an animal, comprising administering to the animal an MMP-13 inhibiting amount of a compound of Formula I, or a pharmaceutically acceptable salt thereof.

A further embodiment is a method for treating a disease mediated by an MMP-13 enzyme, comprising administering to a patient suffering from such a disease an effective amount of a compound of Formula I, or a pharmaceutically acceptable salt thereof.

Another invention embodiment is a method for treating a cancer, comprising administering to a patient suffering from such a disease an anticancer effective amount of a compound of Formula I, or a pharmaceutically acceptable salt thereof.

Another invention embodiment is a method for treating breast carcinoma, comprising administering to a patient suffering from such a disease an anticancer effective amount of a compound of Formula I, or a pharmaceutically acceptable salt thereof.

Another invention embodiment is a method for treating a rheumatoid arthritis, comprising administering to a patient suffering from such a disease an effective amount of a compound of Formula I, or a pharmaceutically acceptable salt thereof.

Another invention embodiment is a method for treating a osteoarthritis, comprising administering to a patient suffering from such a disease an effective amount of a compound of Formula I, or a pharmaceutically acceptable salt thereof.

Another invention embodiment is a method for treating a heart failure, comprising administering to a patient suffering from such a disease an effective amount of a compound of Formula I, or a pharmaceutically acceptable salt thereof.

Another invention embodiment is a method for treating a inflammation, comprising administering to a patient suffering from such a disease an effective amount of a compound of Formula I, or a pharmaceutically acceptable salt thereof.

Another embodiment of the present invention is a process for preparing a compound of Formula I

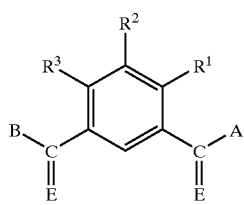

I wherein:
$R^1$, $R^2$, and $R^3$ independently are hydrogen, halo, hydroxy, $C_1$–$C_6$ alkyl, $C_1$–$C_6$ alkoxy, $C_2$–$C_6$ alkenyl, $C_2$–$C_6$ alkynyl, $NO_2$, $RN^4R^5$, CN, or $CF_3$;
E is independently O or S;
A and B independently are $OR^4$ or $NR^4R^5$;

each $R^4$ and $R^5$ independently are H, $C_1$–$C_6$ alkyl, $C_2$–$C_6$ alkenyl, $C_2$–$C_6$ alkynyl, $(CH_2)_n$ aryl, $(CH_2)_n$ cycloalkyl, $(CH_2)_n$ heteroaryl, or $R^4$ and $R^5$ when taken together with the nitrogen to which they are attached complete a 3- to 8-membered ring, optionally containing a heteroatom selected from O, S, or NH, and optionally substituted or unsubstituted;
n is an integer from 0 to 6;
or a pharmaceutically acceptable salt thereof,
the process comprising the step of:
contacting a compound of Formula (A)

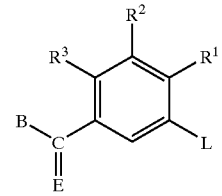

(A)

wherein $R^1$, $R^2$, $R^3$, E, and B are as defined above, and
L is $CO_2H$, $CO_2M$, C(=O)-halo, C(=O)—$OR^7$, C(=O)$NR^8R^9$, C(=O)—C(halo)$_3$, or C≡N,
wherein $R^7$ is pentafluorophenyl, C(=O)$R^4$, wherein $R^4$ is as defined above, or S(O)$_2R^4$, wherein $R^4$ is as defined above;
$R^8$ and $R^9$ are taken together with the nitrogen atom to which they are attached to form imidazol-1-yl, phthalimid-1-yl, benzotriazol-1-yl, or tetrazol-1-yl; and
M is an alkali earth metal cation or alkaline earth metal cation; with a solvent and a compound of Formula (B)

D-$R^4$ (B)

wherein $R^4$ is as defined above and D is HO, HN($R^5$), MO, or MN($R^5$);
wherein $R^5$ and M are as defined above;
optionally in the presence of from 1 to 3 agents selected from: a coupling agent, a tertiary organic amine, an acid catalyst, a base catalyst, an acid halide, and an acid anhydride.

Another invention embodiment is the invention process wherein n is an integer of from 0 to 6 and $R^4$ is $(CH_2)_n$ aryl or $(CH_2)_n$ heteroaryl.

Another invention embodiment is the invention process wherein n is an integer of from 0 to 6;
$R^4$ is $(CH_2)_n$ aryl or $(CH_2)_n$ heteroaryl;
A is $OR^4$; and
B is $OR^4$.

Another invention embodiment is the invention process wherein
$R^4$ is $(CH_2)_n$ aryl or $(CH_2)_n$ heteroaryl;
n is an integer of from 0 to 6;
A is $OR^4$; and
B is $NR^4R^5$, wherein $R^5$ is H or $C_1$–$C_6$ alkyl.

Another invention embodiment is the invention process wherein
$R^4$ is $(CH_2)_n$ aryl or $(CH_2)_n$ heteroaryl;
n is an integer of from 0 to 6;
A is $NR^4R^5$, wherein $R^5$ is H or $C_1$–$C_6$ alkyl; and
B is $OR^4$.

Another invention embodiment is the invention process wherein
$R^4$ is $(CH_2)_n$ aryl or $(CH_2)_n$ heteroaryl;
n is an integer of from 0 to 6;

A is $NR^4R^5$;

B is $NR^4R^5$; and $R^5$ is H or $C_1$–$C_6$ alkyl.

Another invention embodiment is any one of the embodiments of the invention process described above, wherein L is $CO_2H$, $CO_2M$, or C(=O)-halo, wherein M is an alkali earth metal cation or alkaline earth metal cation.

DETAILED DESCRIPTION OF THE INVENTION

The compounds to be used in the method of inhibiting MMP enzymes provided by this invention are those defined by Formula I. In Formula I, $R^1$ to $R^9$ include "$C_1$–$C_6$ alkyl" groups. Alkyl groups are straight and branched carbon chains having from 1 to 6 carbon atoms. Examples of such alkyl groups include methyl, ethyl, isopropyl, tert-butyl, neopentyl, and n-hexyl. The alkyl groups can be substituted if desired, for instance with groups such as hydroxy, amino, alkyl, and dialkylamino, halo, trifluoromethyl, carboxy, nitro, and cyano.

Examples of $NR^4R^5$ groups include amino, methylamino, di-isopropylamino, acetyl amino, propionyl amino, 3-aminopropyl amino, 3-ethylaminobutyl amino, 3-di-n-propylamino-propyl amino, 4-diethylaminobutyl amino, and 3-carboxypropionyl amino. $R^4$ and $R^5$ can be taken together with the nitrogen to which they are attached to form a ring containing from 3 to 7 carbon atoms and 1, 2, or 3 heteroatoms selected from the group consisting of nitrogen, substituted nitrogen, oxygen, and sulfur. Examples of such cyclic $NR^4R^5$ groups include pyrrolidinyl, piperazinyl, 4-methylpiperazinyl, 4-benzylpiperazinyl, pyridinyl, piperidinyl, pyrazinyl, morpholinyl, and the like.

"Halo" includes fluoro, chloro, bromo, and iodo.

"Alkenyl" means straight and branched hydrocarbon radicals having from 2 to 6 carbon atoms and one double bond and includes ethenyl, 3-buten-1-yl, 2-ethenylbutyl, 3-hexen-1-yl, and the like.

"Alkynyl" means straight and branched hydrocarbon radicals having from 2 to 6 carbon atoms and one triple bond and includes ethynyl, 3-butyn-1-yl, propynyl, 2-butyn-1-yl, 3-pentyn-1-yl, and the like.

"Cycloalkyl" means a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, and the like. Also included are rings in which 1 to 3 heteroatoms replace carbons. Such groups are termed "heterocyclyl," which means a cycloalkyl group also bearing at least one heteroatom selected from O, S, or $NR^2$, examples being oxiranyl, pyrrolidinyl, piperidyl, tetrahydropyran, and morpholine.

"Alkoxy" refers to the alkyl groups mentioned above bound through oxygen, examples of which include methoxy, ethoxy, isopropoxy, tert-butoxy, and the like. In addition, alkoxy refers to polyethers such as —O—$(CH_2)_2$—O—$OH_3$, and the like.

"Acyl" means an R group that is a $C_1$–$C_6$ alkyl or aryl (Ar) group bonded through a carbonyl group, i.e., R—C(O)—, where R is alkyl or aryl. For example, acyl includes a $C_1$–$C_6$ alkanoyl, including substituted alkanoyl, wherein the alkyl portion can be substituted by $NR^4R^5$ or a carboxylic or heterocyclic group. Typical acyl groups include acetyl, benzoyl, isonicotinoyl, and the like.

The alkyl, alkenyl, alkoxy, and alkynyl groups described above are optionally substituted, preferably by 1 to 3 groups selected from $NR^4R^5$, phenyl, substituted phenyl, thio $C_1$–$C_6$ alkyl, $C_1$–$C_6$ alkoxy, hydroxy, carboxy, $C_1$–$C_6$ alkoxycarbonyl, acyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$–$C_6$ alkyl or $(CH_2)_n$Ph where n is 1, 2, or 3. Perhalo and polyhalo substitution is also embraced.

Examples of substituted alkyl groups include 2-aminoethyl, acetylmethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, 4-benzoylbutyl, and 2-(4-methylpiperazinyl)ethyl.

Examples of substituted alkynyl groups include 2-methoxyethynyl, 2-benzoylethylyl, 2-ethylsulfanyethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include aminomethoxy, acetoxymethoxy, trifluoromethoxy, 2-diethylaminoethoxy, 2-ethoxycarbonylethoxy, 3-hydroxypropoxy, 6-carboxyhexyloxy, and the like.

Further, examples of substituted alkyl, alkenyl, and alkynyl groups include dimethylaminomethyl, carboxymethyl, 4-dimethylamino-3-buten-1-yl, 5-ethylmethylamino-3-pentyn-1-yl, 4-morpholinobutyl, 4-tetrahydropyrinidylbutyl, 3-imidazolidin-1-ylpropyl, 4-tetrahydrothiazol-3-yl-butyl, phenylmethyl, 3-chlorophenylmethyl, and the like.

The terms "Ar" and "aryl" refer to unsubstituted and substituted aromatic groups. Heteroaryl groups have from 4 to 10 ring atoms, from 1 to 4 of which are independently selected from the group consisting of O, S, and N. Preferred heteroaryl groups have 1 or 2 heteroatoms in a 5- or 6-membered aromatic ring. Mono- and bicyclic aromatic ring systems are included in the definition of aryl and heteroaryl. A bicyclic aryl group is naphthyl for example. Bicyclic heteroaryl groups include indolyl and benzothienyl, to name a few. Preferred substituent groups include alkyl, alkoxy, halo, amino, alkylamino, dialkylamino, CN, $CF_3$, thioalkyl, acyl and hydroxy. Typical aryl and heteroaryl groups include phenyl, 3-chlorophenyl, 2,6-dibromophenyl, pyridyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, morpholinyl, indolyl, benzotriazolyl, indazolyl, pyrrole, pyrazole, imidazole, thiazole, methylenedioxyphenyl, benzo-2,1,3-thiadiazole, benzo-2,1,3-oxadiazole, and the like.

Preferred Ar groups are phenyl and phenyl substituted by 1, 2, or 3 groups independently selected from the group consisting of alkyl, alkoxy, thio, thioalkyl, halo, hydroxy, —$COOR^7$, trifluoromethyl, nitro, amino of the formula —$NR^4R^5$, and $T(CH_2)_mQR^4$ or $T(CH_2)_mCO_2R^4$ wherein m is 1 to 6, T is O, S, $NR^4$, $N(O)R^4$, $NR^4R^6Y$, or $CR^4R^5$, Q is O, S, $NR^5$, $N(O)R^5$, or $NR^5R^6Y$ wherein $R^4$ and $R^5$ are as described above, and $R^7$ is H, alkyl or substituted alkyl, for example, methyl, trichloroethyl, diphenylmethyl, and the like. The alkyl and alkoxy groups can be substituted as defined above. For example, typical groups are carboxyalkyl, alkoxycarbonylalkyl, hydroxyalkyl, hydroxyalkoxy, and alkoxyalkyl. Typical substituted aryl groups include 2,6-dichlorophenyl, 3-hydroxyphenyl, 1,3-benzodioxolyl, 4-dimethylaminophenyl, 2,4,6-triethoxyphenyl, 3-cyanophenyl, 4-methylthiophenyl, and 3,5-dinitrophenyl.

The phrase "tertiary organic amine" means a trisubstituted nitrogen group wherein the 3 substituents are independently selected from $C_1$–$C_{12}$ alkyl, $C_3$–$C_{12}$ cycloalkyl, benzyl, or wherein two of the substituents are taken together with the nitrogen atom to which they are attached to form a 5- or 6-membered, monocyclic heterocycle containing one nitrogen atom and carbon atoms, and the third substituent is selected from $C_1$–$C_{12}$ alkyl and benzyl, or wherein the three substituents are taken together with the nitrogen atom to which they are attached to form a 7- to 12-membered bicyclic heterocycle containing 1 or 2 nitrogen atoms and carbon atoms, and optionally a C=N double bond when 2 nitrogen atoms are present. Illustrative examples of tertiary organic amine include triethylamine, diisopropylethylamine, benzyl diethylamino, dicyclohexylmethyl-amine, 1,8-diazabicycle[5.4.0]undec-7-ene ("DBU"), 1,4-diazabicyclo[2.2.2]octane ("TED"), and 1,5-diazabicycle[4.3.0]non-5-ene.

The term "coupling agent" includes any reagent, or any combination of two, three, or four reagents, conventionally used to promote coupling of a carboxylic acid, or a pharmaceutically acceptable salt thereof, with an alcohol or an amine to yield a carboxylic ester or carboxylic amide, respectively. The coupling agents are described in *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; and the text *Advanced Organic Chemistry*, 5$^{th}$ edition, by Jerry March, Wiley-Interscience, New York (2001). Illustrative examples of coupling agents include N,N'-carbonyldiimidazole ("CDI"), N,N'-dicyclohexylcarbodiimide ("DCC"), triphenylphosphine with diethylazodicarboxylate, bis(2-oxo-3-oxazolidinyl)phosphinic chloride ("BOP-Cl"), $POCl_3$, $Ti(Cl)_4$, and 1-(3-dimethylaminopropyl)-3-ethylcarbodiimide hydrochloride ("EDAC").

The phrase "acid catalyst" means any protic or Lewis acid that is conventionally used to catalyze coupling of a carboxylic acid, or a pharmaceutically acceptable salt thereof, a nitrile, carboxylic ester, carboxylic amide, carboxylic acid halide, or carboxylic acid anhydride with an alcohol or an amine to yield a carboxylic ester or carboxylic amide, respectively. The acid catalysts are described in *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; and the text *Advanced Organic Chemistry*, 5$^{th}$ edition, by Jerry March, Wiley-Interscience, New York (2001). Illustrative examples include anhydrous hydrogen chloride, hydrochloric acid, hydrogen bromide in acetic acid, zinc chloride, titanium tetrachloride, acetic acid, trifluoroacetic acid, phenol, sulfuric acid, methanesulfonic acid, magnesium sulfate, Amberlyst-15 resin, silica gel, and the like.

It should be appreciated that a nitrile may be contacted with an alcohol or an amine in the presence of an acid catalyst, and the resulting intermediate imidate or amidine, respectively, may be contacted with water to yield the carboxylic ester or carboxylic amide, respectively.

The phrase "base catalyst" means any base that is conventionally used to catalyze coupling of a carboxylic acid, or a pharmaceutically acceptable salt thereof, carboxylic ester, carboxylic amide, carboxylic acid halide, or carboxylic acid anhydride with an alcohol or an amine to yield a carboxylic ester or carboxylic amide, respectively. The base catalysts are described in *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; and the text *Advanced Organic Chemistry*, 5$^{th}$ edition, by Jerry March, Wiley-Interscience, New York (2001). Illustrative examples include sodium hydroxide, sodium hydride, potassium tert-butoxide, a tertiary organic amine, titanium tetraisopropoxide, sodium methoxide, sodium acetate, sodium bicarbonate, potassium carbonate, basic alumina, and the like.

The phrase "acid halide" means any carboxylic acid halide or sulfonic acid halide that is conventionally used to catalyze coupling of a carboxylic acid, or a pharmaceutically acceptable salt thereof, with an alcohol or an amine to yield a carboxylic ester or carboxylic amide, respectively. The acid halides are described in *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; and the text *Advanced Organic Chemistry*, 5$^{th}$ edition, by Jerry March, Wiley-Interscience, New York (2001). Illustrative examples include acetyl chloride, trifluoromethanesulfonyl chloride, 2,2-dimethylacetyl bromide, para-toluenesulfonyl chloride, pentafluoro-benzoyl chloride, and the like.

The phrase "acid anhydride" means any carboxylic acid anhydride or sulfonic acid anhydride that is conventionally used to catalyze coupling of a carboxylic acid, or a pharmaceutically acceptable salt thereof, with an alcohol or an amine to yield a carboxylic ester or carboxylic amide, respectively. The acid anhydrides are described in *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; and the text *Advanced Organic Chemistry*, 5$^{th}$ edition, by Jerry March, Wiley-Interscience, New York (2001). Illustrative examples include acetic anhydride, trifluoroacetic anhydride, trifluoromethanesulfonic acid anhydride, pentafluoro-benzoic anhydride, mixed anhydrides like trifluoroacetyloxycarbonylmethyl, and the like.

The term "halide" includes fluoride, chloride, bromide, and iodide.

The phrase "coupling catalyst" means any metal catalyst, preferably a transition metal catalyst, that is conventionally used to catalyze coupling of an aryl halide, aryl trifluoromethanesulfonate, heteroaryl halide, or heteroaryl trifluoromethanesulfonate, or activated derivatives thereof, including arylboronic acids, heteroarylboronic acids, aryl stannanes, heteroarylstannanes, aryl magnesium halides, heteroaryl magnesium halides, aryl lithiums, or heteroaryl lithiums, with an terminal alkyne to yield an arylalkyne or heteroarylalkyne. The coupling catalysts are described in *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; and the text *Advanced Organic Chemistry*, 5$^{th}$ edition, by Jerry March, Wiley-Interscience, New York (2001). Illustrative examples of coupling catalysts include tetrakis(triphenylphosphine)palladium (0), palladium (II) chloride, palladium (II) acetate, iron (III) chloride, Heck reaction catalysts, Suzuki reaction catalysts, Stille reaction catalysts, and the like.

"Effective amount" as used herein means the quantity of compound of Formula I required to inhibit the hydrolytic activity of one or more matrix metalloproteinase enzymes in a mammal.

The term "mammal" includes humans and animals such as dogs, cats, horses, sheep, and cattle. The term "host" means a mammal to which a compound is administered.

The term "patient" means a mammal. Preferred patients include humans, cats, dogs, cows, horses, pigs, and sheep.

The term "animal" means a mammal. Preferred animals include humans, rats, mice, guinea pigs, rabbits, monkeys, cats, dogs, cows, horses, pigs, and sheep.

It should be appreciated that determination of a therapeutically effective treatment regimen for a patient is within the level of ordinary skill in the medical or veterinarian arts. In clinical use, an effective amount may be the amount that is recommended by the U.S. Food and Drug Administration, or an equivalent foreign agency.

The phrase "admixed" or "in admixture" means the ingredients so mixed comprise either a heterogeneous or homogeneous mixture. Preferred is a homogeneous mixture.

The phrases "pharmaceutical preparation" and "preparation" are synonymous unless otherwise indicated, and include the formulation of the active compound with encapsulating material as a carrier providing a capsule in which the active component, with or without other carriers, is surrounded by a carrier, which is thus in association with it. Similarly, cachets and lozenges are included. Pharmaceutical preparations are fully described below.

The phrase "anticancer effective amount" means an amount of invention compound, or a pharmaceutically acceptable salt thereof, sufficient to inhibit, halt, or cause regression of the cancer being treated in a particular patient or patient population. For example in humans or other mammals, an anticancer effective amount can be determined experimentally in a laboratory or clinical setting, or may be the amount required by the guidelines of the United States Food and Drug Administration, or equivalent foreign agency, for the particular cancer and patient being treated.

It should be appreciated that an effective amount of a compound of Formula I, or a pharmaceutically acceptable salt thereof, for treatment of osteoarthritis or rheumatoid arthritis is an amount of invention compound, or a pharmaceutically acceptable salt thereof, sufficient to inhibit, halt, or cause regression of the arthritis being treated in a particular patient or patient population. For example in humans or other mammals, an anti-arthritic effective amount can be determined experimentally in a laboratory or clinical setting, or may be the amount required by the guidelines of the United States Food and Drug Administration, or equivalent foreign agency, for the particular arthritis and patient being treated.

The phrase "MMP-13 inhibiting amount" means an amount of a compound of Formula I, or a pharmaceutically acceptable salt thereof, sufficient to inhibit an enzyme matrix metalloproteinase-13, including a truncated form thereof, including a catalytic domain thereof, in a particular animal or animal population. For example in a human or other mammal, an MMP-13 inhibiting amount can be determined experimentally in a laboratory or clinical setting, or may be the amount required by the guidelines of the United States Food and Drug Administration, or equivalent foreign agency, for the particular MMP-13 enzyme and patient being treated.

It should be appreciated that the matrix metalloproteinases include the following enzymes:

MMP-1, also known as interstitial collagenase, collagenase-1, or fibroblast-type collagenase;

MMP-2, also known as gelatinase A or 72 kDa Type IV collagenase;

MMP-3, also known as stromelysin or stromelysin-1;

MMP-7, also known as matrilysin or PUMP-1;

MMP-8, also known as collagenase-2, neutrophil collagenase, or polymorphonuclear-type ("PMN-type") collagenase;

MMP-9, also known as gelatinase B or 92 kDa Type IV collagenase;

MMP-10, also known as stromelysin-2;

MMP-11, also known as stromelysin-3;

MMP-12, also known as metalloelastase;

MMP-13, also known as collagenase-3;

MMP-14, also known as membrane-type ("MT") 1-IMP or MT1-MMP;

MMP-15, also known as MT2-MMP;

MMP-16, also known as MT3-MMP;

MMP-17, also known as MT4-MMP;

MMP-18; and

MMP-19.

Other MMPs are known, including MMP-26, also known as matrilysin-2.

As discussed above, one aspect of the present invention is a compound or a method that uses a compound of Formula I, or a pharmaceutically acceptable salt thereof, that is a selective inhibitor of the enzyme MMP-13. A selective inhibitor of MMP-13, as used in the present invention, is a compound that is $\geq 5$ times more potent in vitro versus MMP-13 than versus at least one other matrix metalloproteinase enzyme such as, for example, MMP-1, MMP-2, MMP-3, MMP-7, MMP-8, MMP -9, or MMP-14, or versus tumor necrosis factor alpha convertase ("TACE"). A preferred aspect of the present invention is a compound or a method of using a compound that is a selective inhibitor of MMP-13 versus MMP-1. Other preferred embodiments of the present invention are a compound, or methods that use a compound of Formula I, or a pharmaceutically acceptable salt thereof, that is $\geq 10$, $\geq 20$, $\geq 50$, $\geq 100$, or $\geq 1000$ times more potent in vitro against MMP-13 than at least one other MMP enzyme or TACE.

Still other aspects of the present invention are compounds of Formula I, or a pharmaceutically acceptable salt thereof, that are selective inhibitors of MMP-13 versus 2, 3, 4, 5, 6, or 7 other MMP enzymes, or versus TACE and 1, 2, 3, 4, 5, 6, or 7 other MMP enzymes. Still other aspects of the present invention are methods that use the compounds of Formula I, or a pharmaceutically acceptable salt thereof.

Preferred are invention methods that use compounds of Formula I, or a pharmaceutically acceptable salt thereof, wherein the compound or the salt thereof, is embraced by one of the preferred embodiments of a selective inhibitor of MMP-13 described above.

It should be appreciated that determination of proper dosage forms, dosage amounts, and routes of administration, is within the level of ordinary skill in the pharmaceutical and medical arts, and is described below.

The term "$IC_{50}$" means the concentration of test compound required to inhibit activity of a biological target, such as a receptor or enzyme, by 50%.

The phrase "catalytic domain" means the domain containing a catalytic zinc cation of the MMP enzyme, wherein the MMP enzyme contains two or more domains. A catalytic domain includes truncated forms thereof that retain at least some of the catalytic activity of MMP-13 or MMP-13CD against any one of a number of known naturally-occurring or synthetic substrates. For example, the collagenases, of which MMP-13 is a member, have been reported to contain a signal peptide domain, a propeptide domain, a catalytic domain, and a hemopexin-like domain (Ye Qi-Zhuang, Hupe D., Johnson L., *Current Medicinal Chemistry*, 1996; 3:407–418).

The phrase "a method for inhibiting an MMP-13 enzyme" includes methods of inhibiting full length MMP-13, truncated forms thereof that retain catalytic activity against any one of a number of known naturally-occurring or synthetic substrates, including forms that contain the catalytic domain of MMP-13, as well as the catalytic domain of MMP-13 alone, and truncated forms of the catalytic domain of MMP-13 that retain at least some catalytic activity.

It should be appreciated that it has been shown previously (Ye Qi-Zhuang, et al., supra., 1996) that inhibitor activity against a catalytic domain of an MMP is predictive of the inhibitor activity against the respective full-length enzyme.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention.

The compounds of Formula I may have chiral centers, and thus can exist as racemic mixtures and individual enantiomers. All such isomeric forms can be used in the method of this invention and are provided as new compounds.

The compounds of Formula I are capable of further forming both pharmaceutically acceptable formulations comprising salts, including but not limited to acid addition and/or base salts, solvents and N-oxides of a compound of Formula I. This invention also provides pharmaceutical formulations comprising a compound of Formula I together with a pharmaceutically acceptable carrier, diluent, or excipient. All of these forms can be used in the method of the present invention and are provided as new pharmaceutical compositions.

Pharmaceutically acceptable acid addition salts of the compounds of Formula I include salts derived form inorganic acids such as hydrochloric, nitric, phosphoric, sulfuric, hydrobromic, hydroiodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, actate, maleate, tartrate, methanesulfonate, and the like. Also contemplated are the salts of amino acids such as arginate, gluconate, galacturonate, and the like; see, for example, Berge et al., "Pharmaceutical Salts," *J. of Pharmaceutical Science*, 1977;66: 1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge et al., supra., 1977.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

The compounds of the present invention can be formulated and administered in a wide variety of oral and parenteral dosage forms, including transdermal and rectal administration. All that is required is that an MMP inhibitor be administered to a mammal suffering from a disease in an effective amount, which is that amount required to cause an improvement in the disease and/or the symptoms associated with such disease. It will be recognized to those skilled in the art that the following dosage forms may comprise as the active component, either a compound of Formula I or a corresponding pharmaceutically acceptable salt or solvate of a compound of Formula I.

A compound of Formula I, or a pharmaceutically acceptable salt thereof, may be prepared by one of ordinary skill in the art of organic chemistry by procedures found in the chemical literature such as, for example, *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; the text *Advanced Organic Chemistry*, 5$^{th}$ edition, by Jerry March, Wiley-Interscience, New York (2001); or the *Handbook of Heterocyclic Chemistry*, by Alan R. Katritzky, Pergamon Press Ltd., London, (1985), to name a few. Alternatively, a skilled artisan may find methods useful for preparing the invention compounds in the chemical literature by searching widely available databases such as, for example, those available from the *Chemical Abstracts Service*, Columbus, Ohio, or *MDL Information Systems GmbH* (formerly Beilstein Information Systems GmbH), Frankfurt, Germany.

Preparations of the compounds of the present invention may use starting materials, reagents, solvents, and catalysts that may be purchased from commercial sources or they may be readily prepared by adapting procedures in the references or resources cited above. Commercial sources of starting materials, reagents, solvents, and catalysts useful in preparing invention compounds include, for example, *The Aldrich Chemical Company*, and other subsidiaries of Sigma-Aldrich Corporation, St. Louis, Mo., BACHEM, BACHEM A.G., Switzerland, or *Lancaster Synthesis Ltd.*, United Kingdom.

*Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience;

the text *Advanced Organic Chemistry*, 5th edition, by Jerry March, Wiley-Interscience, New York (2001); and the *Handbook of Heterocyclic Chemistry*, by Alan R. Katritzky, Pergamon Press Ltd., London, (1985) are hereby incorporated by reference.

as dichloromethane to give a resin-bound amide. The resin is then cleaved by reaction with an amine, $NHR^4R^5$, in dioxane in the presence of an organic base to give a bis-amide of Formula I, wherein each $R^4$ and $R^5$ independently are as defined above.

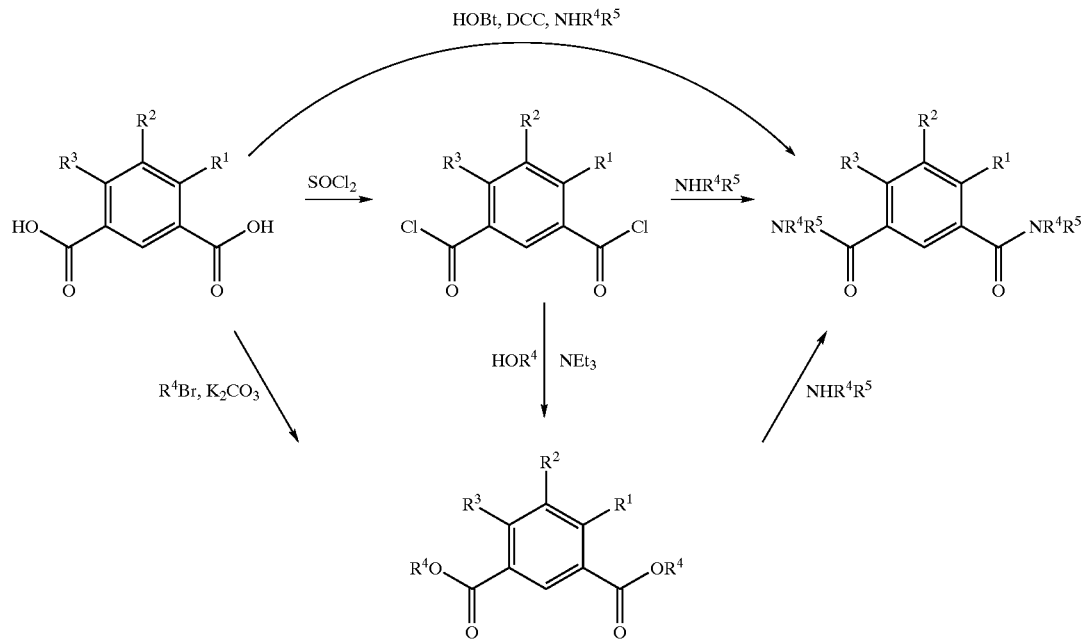

Scheme 1

The invention compounds are prepared by methods well-known to those skilled in the art of organic chemistry. The compounds of Formula I are prepared utilizing commercially available starting materials, or reactants that are readily prepared by standard organic synthetic techniques. A typical synthesis of the invention compounds of Formula I is shown in Scheme 1 below. The first step in Scheme 1 comprises reacting a diacid with a chlorinating reagent such as thionyl chloride or oxalyl chloride in a nonprotic solvent such as dichloromethane to give the diacid chloride. This acid chloride can then be reacted with an amine, $NHR^4R^5$, in excess or with an organic base such as triethylamine, to give a bis-amide of Formula I. Alternately, the acid chloride can be reacted with an alcohol, $R^4OH$, in a nonprotic solvent such as dichloromethane along with an organic or inorganic base such as triethylamine or potassium carbonate to give a bis-ester of Formula I. The bis-ester can in some circumstances be reacted with an amine, $NHR^4R^5$, at elevated temperatures to give a bis-amide of Formula I. The diacid can also be reacted with an alkyl halide in a nonprotic solvent containing an organic or inorganic base to give a bis-ester of Formula I. A third sequence involves the reaction of the diacid with hydroxybenzotriazole, HOBt, and dicyclohexylcarbodiimide, DCC, and an amine, $NHR^4R^5$, in a solvent such as dimethylformamide, DMF, or dichloromethane to give a bis-amide of Formula I.

Compounds of Formula I have also been synthesized using combinatorial techniques, Scheme 2. The diacid chloride is bound to a resin such as Marshall resin to give a bound acid chloride. This is then reacted with an amine, $NHR^4R^5$, in the presence of triethylamine in a solvent such

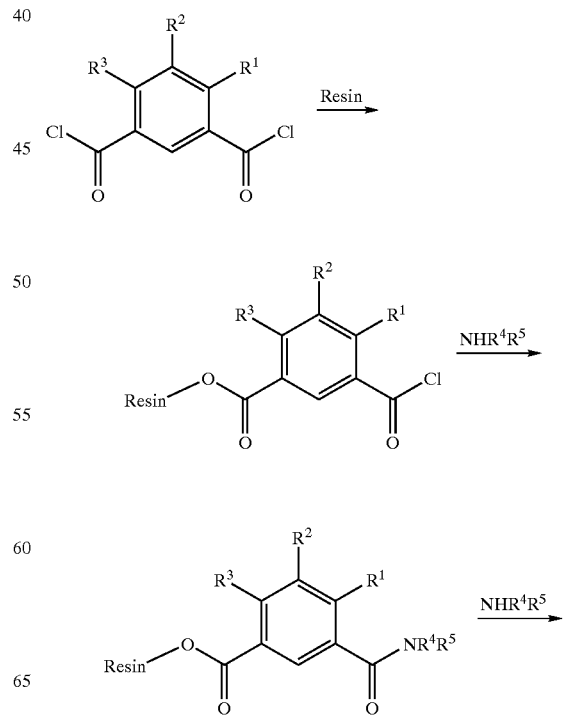

Scheme 2

-continued

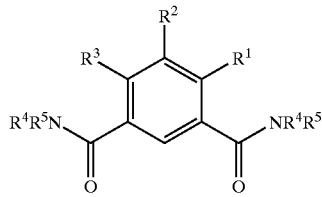

During the synthesis of some of the invention compounds, it may be desirable to protect reactive functional groups such as hydroxy, amino, and carboxylic groups, so as to avoid unwanted side reactions. The use of protecting groups in synthetic organic chemistry is well-established and is fully described by Greene and Wuts in "Protecting Groups in Organic Synthesis" (John Wiley & Son Press, $3^{rd}$ ed). Examples of common amino protecting groups include acyl groups such as formyl and acetyl, and arylalkyl groups such as benzyl. Typical hydroxy protecting groups include ether forming groups such as methyl and ethyl, and acyl groups such as acetyl and tert-butoxycarbonyl (tBOC). Carboxylic acids generally are protected as esters, for example, 2,2,2-trichloroethyl and benzyl. These protecting groups are readily cleaved by standard methods when desired.

The following detailed examples further illustrate the synthesis of typical invention compounds of Formula I. The examples are representative only, and are not to be construed as limiting the invention in any respect.

EXAMPLE 1

4-Methoxy-N,N'-bis-(4-methoxybenzyl)-isophthalamide

To a solution of triethyl amine (1.212 g, 12 mmol) and 4-methoxy-benzyl amine (1.37 g, 10 mmol) in methylene chloride (50 mL) was added in parts 4-methoxy-1,3-benzenedicarbonyl dichloride (1.16 g, 5.0 mmol). The mixture was stirred at room temperature 18 hours. The solution was washed successively with 10% citric acid (100 mL), 1N sodium hydroxide solution (100 mL), and then brine (100 mL). The organic phase was dried over magnesium sulfate and evaporated at reduced pressure to give 1.95 g (90%) of the bisamide as a white solid. MS: M+1=435.

Microanalysis ($C_{25}H_{26}N_2O_5$):
Calc'd: C, 69.11; H, 6.03; N, 6.45. Found: C, 68.82; H, 5.99; N, 6.27.

EXAMPLE 2

N,N'-Dibenzyl-4-methoxy-isophthalamide

By following the general method of Example 1, benzyl amine was reacted with 4-methoxy-1,3-benzenedicarbonyl dichloride to give the titled compound. MS: M+1=375.2.
Microanalysis ($C_{23}H_{22}N_2O_3$):
Calc'd: C, 73.78; H, 5.92; N, 7.48. Found: C, 73.37; H, 6.04; N, 7.54.

EXAMPLE 3

Isophthalic acid di-(2,1,3-benzothiadiazol-5-yl)methyl ester

By following the general method of Example 1, 1,3-benzenedicarbonyl chloride was reacted with 2,1,3-benzothiadiazol-5-ylmethanol to provide isophthalic acid di-(2,1,3-benzothiadiazol-5-yl)methyl ester. MS: M+1=463.
Microanalysis ($C_{22}H_{14}N_4O_4S_2$.0.2 $H_2O$):
Calc'd: C, 59.69; H, 2.91; N, 11.87. Found: C, 59.69; H, 3.11; N, 12.02.

EXAMPLE 4

4-Methoxy-isophthalic acid dibenzyl ester

To a solution of diisopropyl ethyl amine (5.17 g, 40 mmol) and benzyl alcohol (4.33 g, 40 mmol) in methylene chloride (100 mL) was added in parts 4-methoxy-1,3-benzenedicarbonyl dichloride (4.03 g, 17.3 mmol). The mixture was stirred at room temperature 24 hours. The solution was washed successively with water (100 mL), 1N hydrochloric acid (100 mL), saturated sodium bicarbonate solution (100 mL), and then brine (100 mL). The organic phase was dried over magnesium sulfate and evaporated at reduced pressure to give an oil. The oil was purified using prep medium pressure liquid chromatography ("MPLC") (90 g silica gel, 3:1 [hexane/ethyl acetate]) to give 2.99 g (46%) of a thick clear oil. MS: M+1=377.2.
Microanalysis ($C_{23}H_{20}O_5$):
Calc'd: C, 73.39; H, 5.36; N, 0. Found: C, 73.29; H, 5.74; N, 0.

EXAMPLE 5

4-Methoxy-isophthalic acid dipyridin-4-ylmethyl ester

In N,N-dimethylformamide ("DMF") (25 mL) was stirred 4-methoxy-1,3-benzenedicarboxylic acid (675 mg, 3.4 mmol) and potassium carbonate (4.3 g, 31 mmol). To this was added in parts, picolyl chloride hydrochloride (1.23 g, 7.5 mmol). The mixture was stirred at room temperature 24 hours. The mixture was filtered free of insoluble material and the DMF solution evaporated at reduced pressure to give a solid. This was partitioned between methylene chloride (100 mL) and saturated sodium bicarbonate solution (100 ML). The organic phase was separated and washed with water (100 mL) and then brine (100 mL). The organic phase was dried over magnesium sulfate and evaporated at reduced pressure to give 0.619 g (48%) of a tan solid. MS: M+1=379.1.
Microanalysis ($C_{21}H_{18}N_2O_5$):
Calc'd: C, 66.66; H, 4.79; N, 7.40. Found: C, 66.15; H, 4.94; N, 7.53.

EXAMPLE 6

5-Nitro-isophthalic acid dibenzyl ester

In DMF (60 mL) was stirred 5-nitro-1,3-benzenedicarboxylic acid (2.1 g, 10 mmol) and potassium carbonate (8.3 g, 60 mmol). To this was added benzyl bromide (3.60 g, 21 mmol) and the mixture stirred at room temperature for 18 hours. The mixture was then filtered free of solids and the DMF solution evaporated at reduced pressure to give an oil. The oil was partitioned between methylene chloride (100 mL) and 10% citric acid solution (100 mL). The organic phase was separated, washed successively with saturated sodium bicarbonate solution (100 mL) and then brine (100 mL). The organic phase was dried over magnesium sulfate and evaporated at reduced pressure to give 1.5 g (39%) of the solid diester. MS: M-benzyl=300.1.

Microanalysis ($C_{22}H_{17}NO_6$):
Calc'd: C, 67.52; H, 4.38; N, 3.58. Found: C, 67.55; H, 4.56; N, 3.38.

EXAMPLE 7

5-Amino-isophthalic acid dibenzyl ester

In acetic acid (15 mL) was stirred 5-nitroisophthalic acid dibenzyl ester (1.3 g, 3.3 mmol). To this was added in parts zinc dust (1.75 g, 26.6 mmol). The mixture was stirred at room temperature for 18 hours. The mixture was filtered free of insoluble material and the acetic acid solution evaporated at reduced pressure. This residue was dissolved in ethyl acetate (120 mL) and washed successively with saturated sodium bicarbonate solution (50 mL), water (50 mL), and brine (50 mL). The organic phase was dried over magnesium sulfate and evaporated in vacuo to give a solid. The solid was stirred into ether (75 mL) and brought to reflux. The solution allowed to recrystallize to give 260 mg (22%) of a white solid. MS: M+1=362.2.

Microanalysis ($C_{22}H_{19}NO_4$):
Calc'd: C, 73.11; H, 5.30; N, 3.88. Found: C, 72.80; H, 5.40; N, 3.74.

EXAMPLE 8

Isophthalic acid bis-(4-fluoro-benzyl) ester

4-Fluorobenzyl alcohol (1.26 g) is added to isophthaloyl dichloride (1.015 g) in toluene (100 mL). Triethylamine (1.01 g) is added, and the reaction mixture is stirred at room temperature for 5 days. The reaction mixture is filtered to remove triethylamine hydrochloride. The filtrate is evaporated at reduced pressure to give a colorless oil, which crystallized from methanol. Recrystallization from methanol gives the product (1.05 g), mp 78–79° C.

EXAMPLES 9–14

The following compounds were prepared by the general method of Example 8:

EXAMPLE 9

Isophthalic Acid dibenzyl ester, mp 80–82° C.

EXAMPLE 10

N,N'-Bis-(4-chloro-benzyl)-isophthalamide, mp 136–138° C.

EXAMPLE 11

Isophthalic acid bis-(3-fluoro-benzyl) ester, mp 81–82° C.

EXAMPLE 12

Isophthalic acid bis-(4-methoxy-benzyl) ester, mp 90–92° C.

EXAMPLE 13

Isophthalic acid bis-(3-methoxy-benzyl) ester, mp 68–70° C.

EXAMPLE 14

Isophthalic acid bis-(1,3-benzodioxol-5-ylmethyl) ester, mp 109–110° C.

EXAMPLE 15

N,N'-Bis-(4-fluoro-benzyl)-isophthalamide

4-Fluoro-benzylamine (1.25 g) is added to isophthaloyl dichloride (1.015 g) in toluene (100 mL). The reaction mixture is stirred at room temperature for 4 days. The product is filtered off and washed with toluene. Recrystallization from methanol gives the product (0.52 g), mp 190–191° C.

EXAMPLES 16–18

By following the general method of Example 15, the following compounds were prepared:

EXAMPLE 16

N,N'-Bis-(4-methoxy-benzyl)-isophthalamide, mp 175–176° C.

EXAMPLE 17

N,N'-Bis-(3-fluoro-benzyl)-isophthalamide, mp 138–140° C.

EXAMPLE 18

N,N'-Bis-(3-chloro-benzyl)-isophthalamide, mp 128–130° C.

EXAMPLE 19

N,N'-Bis-1,3-benzodioxol-5-ylmethyl-isophthalamide

In methylene chloride (200 mL) was dissolved the piperonyl amine (12.8 g, 85 mmol) and triethyl amine (9.09 g, 90 mmol). To this was added in parts 1,3-benzenedicarbonyl dichloride (8.12 g, 40 mmol). The mixture was stirred at room temperature for 24 hours and then diluted with 1N hydrochloric acid (300 mL). The mixture was filtered to collect a solid. The solid was washed with 1N sodium hydroxide (50 mL) and then water (6×100 mL). The solid was dried at 65° C. for 3 hours at reduced pressure to give 15.08 g (87%) of a white solid. MS: M+1=433.3.

Microanalysis ($C_{24}H_{20}N_2O_6$):
Calc'd: C, 66.66; H, 4.66; N, 6.48. Found: C, 66.56; H, 4.75; N, 6.46.

EXAMPLE 20

4-Acetyl-isophthalic acid dibenzyl ester

In dioxane was placed 4-bromo-1,3-benzenedicarboxylate dibenzyl ester (1.78 g, 4.2 mmol), tri-n-butyl(1-ethoxyvinyl), tin (1.70 g, 4.7 mmol), and bis-triphenylphosphine palladium (II) dichloride (175 mg, 0.25 mmol). The mixture was warmed to 100° C. and stirred for 24 hours. The dark solution was evaporated at reduced pressure to give an oil. The oil was purified by MPLC (90 g silica gel, 3:1 [hexane: ethyl acetate]). This gave 0.91 g of the ethoxyvinyl intermediate. This was then placed into a solution of acetic acid (25 mL) and water (5%) and stirred for 1 hour. The mixture was evaporated in vacuo to give an oil which was purified by MPLC (90 g silica gel, 8:2 [hexane: ethyl acetate]). This gave 699 mg (43%) of a white solid. MS: M+1=389.2.

Microanalysis ($C_{24}H_{20}O_5$):

Calc'd: C, 74.21; H, 5.19; N, 0. Found: C, 73.88; H, 5.81; N, 0.

EXAMPLE 21

4-Methoxycarbonylmethoxy-isophthalic acid dibenzyl ester

In DMF (15 mL) was stirred 4-hydroxy-1,3-benzenedicarboxylate dibenzyl ester (500 mg, 1.4 mmol) and potassium carbonate (276 mg, 2.0 mmol). To this was added methylbromoacetate (230 mg, 1.5 mmol) and the solution warmed to 50° C. and stirred 120 hours. The mixture filtered free of insoluble material and the DMF solution evaporated at reduced pressure to give a red oil. The oil was dissolved in ethyl acetate (50 mL) and washed successively with 10% citric acid (50 ML), saturated sodium bicarbonate solution (50 mL), and brine (50 mL). The organic phase dried over magnesium sulfate and evaporated at reduced pressure to give an oil. The oil was purified by MPLC (90 g silica gel, 2:1[hexane:ethyl acetate]) to give 330 mg (54%) of a clear oil. MS: M+1=435.2.

Microanalysis ($C_{25}H_{22}O_7$):

Calc'd: C, 69.12; H, 5.10; N, 0. Found: C, 68.90; H, 4.99; N, 0.

EXAMPLES 22–44

General Procedures Used in the Combinatorial Array, Examples 22 to 44

Loading of the Resin:

Marshall resin (15.2 g, 21.25 mmol) was swollen in dichloromethane ("DCM") (300 mL) in a 500-mL resin tube (CAUTION: Slightly exothermic, the DCM will nearly boil). Once the mixture cools, cap the tube and agitate slowly for 5 minutes, venting frequently. Drain the DCM to waste. Repeat this wash two additional times. The resin was resuspended in DCM (300 mL) and triethylamine ("TEA") (3.2 g, 32 mmol, 1.5 eq) was added slowly. The resulting mixture was swirled for 5 minutes when isophthalic acid dichloride (17.2 g, 85 mmol, 4 eq) was added in one portion. The resin tube was capped and carefully secured in a wrist shaker, and inverted for 36 hours.

After 36 hours, a slight darkening of the resin was noted. The reaction solvent was drained and the resin washed three times with DCM (200 mL) and two times with diethyl ether (200 mL). The resin was dried in vacuo for 24 hours. Loading was determined both by weight gain and by total chloride determination. [Nitrogen content showed <0.05% N and therefore the absence of triethylamine hydrochloride ("TEA·HCl")]. Typical loading was 1.1 mmol/g.

Resin Distribution:

Calibrate the Miniblock resin loader for each resin used in the protocol. Record the milligram resin added per well, and calculate the number of millimoles per well. Using this calibration and the loading for each resin, distribute 0.15 mmol of resin per reaction tube. Close the valve on the block.

Amine solution prep:

Dilute the $R^1$ amine set to 0.5 M in DCM. Prepare a 0.2-M solution of TEA in DCM (1.5 mL per reaction). Prepare a 0.2-M solution of TEA in dioxane (1.5 mL per reaction). Dilute the $R^2$ amine set to 0.5 M in dioxane.

Addition of amine $R^1$:

Add TEA solution in DCM from Step 2 (1.5 mL) to each reaction tube, then using the Miniblock Map as a guide, distribute the appropriate $R^1$ amine (315 μL, 1.05 eq). Shake for 24 hours. After 24 hours, place the reaction block on a filtration station without a collection block and drain the reactions to waste. Close the valve, add 2 mL DCM, shake for 2 minutes, again draining to waste. Unless Step 4 is to be carried out immediately, store the reaction blocks under vacuum.

Addition of Amine $R^2$/Resin Cleavage:

Add TEA solution in dioxane from Step 2 (1.5 mL) to each reaction tube, then using the Miniblock Map as a guide, distribute the appropriate $R^2$ amine (300 μL, 1.05 eq). Shake for 72 hours. After 72 hours, place the reaction block on a filtration station with a labeled collection block and drain the reactions. Close the valve, add 2 mL DCM, shake for 2 minutes, drain into the collection tubes.

Analysis:

Check 25% by loop mass spectrometry ("MS"), first evaporating the DCM from the MS samples. If <90% pass, then ask for assistance.

Concentrate:

Concentrate the crude samples in the Genevac and submit.

EXAMPLE 22

N,N'-Bis-1,3-benzodioxol-5-ylmethyl-4-methoxy-isophthalamide

MS: Calc'd, 462.1; found, 463; high performance liquid chromatography ("HPLC") purity, 100%.

EXAMPLE 23

N-1,3-Benzodioxol-5-ylmethyl-4-methoxy-N'-(4-methoxy-benzyl)-isophthalamide

MS: Calc'd, 448.5; found, 449; HPLC purity, 100%.

EXAMPLE 24

4-Methoxy-N,N'-bis-(4-methoxy-benzyl)-isophthalamide

MS: Calc'd, 448.5; found, 449; HPLC purity, 100%.

EXAMPLE 25

N-1,3-Benzodioxol-5-ylmethyl-N'-(4-chloro-benzyl)-4-methoxy-isophthalamide

MS: Calc'd, 452.9; found, 452; HPLC purity, 100%.

EXAMPLE 26

N-Benzyl-4-methoxy-N'-(4-methoxy-benzyl)-isophthalamide

MS: Calc'd, 404.47; found, 405; HPLC purity, 100%.

EXAMPLE 27

N'-Benzyl-4-methoxy-N-(4-methoxy-benzyl)-isophthalamide

MS: Calc'd, 404.18; found, 405; HPLC purity, 75%.

EXAMPLE 28

N,N'-Bis-1,3-benzodioxol-5-ylmethyl-isophthalamide

MS: Calc'd, 432.3; found, 433; HPLC purity, 100%.

EXAMPLE 29

4-Methoxy-N-(4-methoxy-benzyl)-N'-pyridin-4-ylmethyl-isophthalamide

MS: Calc'd, 405.1; found, 406; HPLC purity, 100%.

EXAMPLE 30

N,N'-Bis-(3-methoxy-benzyl)-isophthalamide

MS: Calc'd, 404.2; found, 405; HPLC purity, 100%.

EXAMPLE 31

N-1,3-Benzodioxol-5-ylmethyl-N'-benzyl-isophthalamide

MS: Calc'd, 388.3; found, 389; HPLC purity, 90%.

EXAMPLE 32

N-1,3-Benzodioxol-5-ylmethyl-N'-(4-methoxy-benzyl)-isophthalamide

MS: Calc'd, 418.1; found, 419; HPLC purity, 82%.

EXAMPLE 33

N,N'-Dibenzyl-4-methoxy-isophthalamide

MS: Calc'd, 374.2; found, 375; HPLC purity, 100%.

EXAMPLE 34

N-Benzyl-N'-(4-methoxy-benzyl)-isophthalamide

MS: Calc'd, 374.1; found, 375; HPLC purity, 77%.

EXAMPLE 35

N'-1,3-Benzodioxol-5-ylmethyl-4-methoxy-N-(2-phenoxy-ethyl)-isophthalamide

MS: Calc'd, 448.3; found, 449; HPLC purity, 91%.

EXAMPLE 36

N-1,3-Benzodioxol-5-ylmethyl-4-methoxy-N'-(2-phenoxy-ethyl)-isophthalamide

MS: Calc'd, 448.1; found, 449.21; HPLC purity, 88%.

EXAMPLE 37

N-1,3-Benzodioxol-5-ylmethyl-N'-furan-2-ylmethyl-isophthalamide

MS: Calc'd, 378.1; found, 379; HPLC purity, 87%.

EXAMPLE 38

N'-1,3-Benzodioxol-5-ylmethyl-N-(2-ethoxy-ethyl)-4-methoxy-isophthalamide

MS: Calc'd, 400.2; found, 401; HPLC purity, 100%.

EXAMPLE 39

N,N'-Bis-(4-methoxy-benzyl)-isophthalamide

MS: Calc'd, 372.3; found, 373; HPLC purity, 100%.

EXAMPLE 40

N,N'-Bis-(3-hydroxymethyl-phenyl)-isophthalamide

MS: Calc'd, 376.1; found, 377; HPLC purity, 70%.

EXAMPLE 41

N-Benzyl-4-methoxy-N'-(2-phenoxy-ethyl)-isophthalamide

MS: Calc'd, 404.22; found, 405; HPLC purity, 89.9%.

EXAMPLE 42

4-Methoxy-N,N'-bis-(4-methyl-benzyl)-isophthalamide

MS: Calc'd, 402.2; found, 403; HPLC purity, 100%.

EXAMPLE 43

4-Methoxy-N,N'-bis-(3-methoxy-benzyl)-isophthalamide

MS: Calc'd, 434.19; found, 435; HPLC purity, 100%.

EXAMPLE 44

N-1,3-Benzodioxol-5-ylmethyl-4-methoxy-N'-(4-methoxy-benzyl)-isophthalamide

MS: Calc'd, 448.22; found, 449; HPLC purity, 100%.

EXAMPLE 45

4-Amino-N1,N3-bis-1,3-benzodioxol-5-ylmethyl-isophthalamide

The title compound was synthesized in the same manner as Example 19. Microanalysis ($C_{24}H_{21}N_3O_6$): Calc'd: C=64.42, H=4.73, N=9.39; Found: C=64.49, H=4.83, N=9.50.

EXAMPLE 46

4-Acetylamino-N1,N3-bis-1,3-benzodioxol-5-ylmethyl-isophthalamide

The title compound was synthesized in the same manner as Example 19. Microanalysis ($C_{26}H_{23}N_3O_7$): Calc'd: C=63.80, H=4.74, N=8.58; Found: C=63.84, H=4.81, N=8.42.

EXAMPLE 47

N-(3-Methoxy-benzyl)-N'-pyridin-3-ylmethyl-isophthalamide

The title compound was synthesized in the same manner as Example 19. Microanalysis ($C_{22}H_{21}N_3O_3.0.25\ H_2O$): Calc'd: C=69.54, H=5.70, N=11.06. Found: C=69.46, H=5.64, N=10.86.

EXAMPLE 48

N-(3-Methoxy-benzyl)-N'-pyridin-4-ylmethyl-isophthalamide

The title compound was synthesized in the same manner as Example 19. Microanalysis ($C_{22}H_{21}N_3O_3.0.35\ H_2O$): Calc'd: C=69.22, H=5.73, N=11.01. Found: C=69.21, H=5.58, N=10.88.

EXAMPLE 49

N1-1,3-Benzodioxol-5-ylmethyl-N3-pyridin-3-ylmethyl-isophthalamide

The title compound was synthesized in the same manner as Example 19. Microanalysis ($C_{22}H_{19}N_3O_4.0.15\ H_2O$): Calc'd: C=67.38, H=4.96, N=10.72. Found: C=67.86, H=4.76, N=10.55.

EXAMPLE 50

N-(4-Chloro-benzyl)-N'-(3-methoxy-benzyl)-isophthalamide

The title compound was synthesized in the same manner as Example 19. Microanalysis ($C_{23}H_{21}ClN_2O_3.0.25\ H_2O$): Calc'd: C=66.82, H=5.24, N=6.78. Found: C=66.77, H=5.14, N=6.53.

EXAMPLE 51

N-(3,4-Dichloro-benzyl)-N'-(3-methoxy-benzyl)-isophthalamide

The title compound was synthesized in the same manner as Example 19. Microanalysis ($C_{23}H_{20}Cl_2N_2O_3.0.15\ H_2O$): Calc'd: C=61.93, H=4.58, N=6.28. Found: C=61.73, H=4.53, N=6.14.

EXAMPLE 52

N-(4-Methoxy-benzyl)-N'-(3-methoxy-benzyl)-isophthalamide

The title compound was synthesized in the same manner as Example 19. Microanalysis ($C_{24}H_{24}N_2O_4.0.15\ H_2O$): Calc'd: C=70.79, H=6.02, N=6.88. Found: C=70.73, H=6.05, N=6.64.

EXAMPLE 53

N-(3-Methoxy-benzyl)-N'-(4-methyl-benzyl)-isophthalamide

The title compound was synthesized in the same manner as Example 19. Microanalysis ($C_{24}H_{24}N_2O_3.0.2\ H_2O$): Calc'd: C=73.51, H=6.27, N=7.15. Found: C=73.43, H=6.40, N=6.96.

EXAMPLE 54

N,N'-Bis-(4-fluoro-3-methoxy-benzyl)-isophthalamide

The title compound was synthesized in the same manner as Example 19. Microanalysis ($C_{24}H_{22}F_2N_2O_4.0.2\ H_2O$): Calc'd: C=64.91, H=5.09, N=6.31. Found: C=64.78, H=5.09, N=5.98.

EXAMPLE 55

({3-[(1,3-Benzodioxol-5-ylmethyl)-carbamoyl]-benzoyl}-benzyl-amino)-acetic acid

To a solution of N-benzo[1,3]dioxol-5-ylmethyl-isophthalamic acid (3.0 g, 10 mmol) in methylene chloride was added 1-hydroxy-benzotriazole monohydrate ("HOBt") (1.35 g, 10 mmol) and ethyl N-benzylglycine (1.94 g, 10 mmol). To this was added 1-(3-dimethylamino-propyl)-3-ethylcarbodiimide hydrochloride ("EDAC") (1.92 g, 10 mmol) and the mix stirred at room temperature for 24 hours. The solution treated with water (150 mL) and the organic phase separated, washed with 10% citric acid (100 mL), saturated sodium bicarbonate (100 mL) and brine (100 mL). The organic phase dried over magnesium sulfate and evaporated at reduced pressure to give ({3-[(1,3-benzodioxol-5-ylmethyl)-carbamoyl]-benzoyl}-benzyl-amino)-acetic acid ethyl ester as a solid, 3.69 g. To a solution of this ester (3.6 g, 7.6 mmol) in a mix of water (15 mL), dioxane (60 mL) and ethanol (20 mL) was added sodium hydroxide (0.72 g, 18 mmol). The mixture stirred at 50° C. for 24 hours. The solution cooled to room temperature and evaporated at reduced pressure free of solvents. The residue was diluted with water (100 mL) and washed with ether (2×50 mL). The ether discarded and the aqueous phase made acidic with 6N HCl. This was extracted with ethyl acetate (2×100 mL). The organic phases washed with brine (100 mL) and dried over magnesium sulfate. The solvent was evaporated at reduced pressure to give the title compound, 3.41 g. Microanalysis ($C_{25}H_{22}N_2O_6.0.3\ H_2O$): Calc'd: C=66.45, H=5.05, N=6.20. Found: C=66.25, H=5.15, N=5.99.

EXAMPLE 56

N-Benzo[1,3]dioxol-5-ylmethyl-isophthalamic(4-hydroxymethyl-benzoic acid) ester

To a solution of N-benzo[1,3]dioxol-5-ylmethyl-isophthalamic acid (3.0 g, 10 mmol) in DMF (20 mL) was added 4-bromomethylbenzoic acid t-butyl ester (0.77 g, 2.84 mmol) and cesium carbonate (1.14 g, 3.5 mmol). The mixture was warmed to 40° C. and stirred for 18 hours. The solution was cooled to room temperature and filtered free of insolubles. The DMF was then evaporated at reduced pressure to give an oil. The oil was partitioned between ethyl acetate (100 mL) and water (100 mL). The organic phase separated and washed successively with water (100 mL) and brine (50 mL). The organic phase dried over magnesium sulfate and evaporated at reduced pressure to give an oil. The oil was purified by MPLC (90 g silica gel column, 9:1 (methylene chloride/ethyl acetate)) to give N-benzo[1,3] dioxol-5-ylmethyl-isophthalamic(4-hydroxymethyl-benzoic acid t-butyl ester) ester as a white solid, 910 mg. This ester (790 mg, 1.61 mmol) was then dissolved in TFA (8 mL) with anisole (175 mg, 1.61 mmol) and stirred at room temperature for 3 hours. The TFA was evaporated at reduced pressure to give a thick oil. The oil was triturated repeatedly with pet ether (3×20 mL) to give a white solid which was dried at 65° C. for three hours. This gave the title compound 0.671 g. Microanalysis ($C_{24}H_{19}NO_7$.0.13 $H_2O$): Calc'd: C=66.14, H=4.46, N=3.21. Found: C=65.72, H=4.27, N=2.99.

EXAMPLE 57

N-(3,4-Dichloro-benzyl)-N'-pyridin-4-ylmethyl-isophthalamide

The title compound was synthesized in the same manner as Example 19. Microanalysis ($C_{21}H_{17}Cl_2N_3O_2$.0.4 $H_2O$): Calc'd: C=59.84, H=4.26, N=9.97. Found: C=59.86, H=4.17, N=9.87.

EXAMPLE 58

N-(3-Methoxy-benzyl)-N'-(4-nitro-benzyl)-isophthalamide

The title compound was synthesized in the same manner as Example 19. Microanalysis ($C_{23}H_{21}N_3O_5$): Calc'd: C=65.86, H=5.05, N=10.02. Found: C=65.96, H=5.03, N=9.91.

EXAMPLE 59

4-{[3-(3-Methoxy-benzylcarbamoyl)-benzoylamino]-methyl}-benzoic acid methyl ester The title compound was synthesized in the same manner as Example 19. Microanalysis ($C_{25}H_{24}N_2O_5$.0.25 $H_2O$): Calc'd: C=68.71, H=5.65, N=6.41. Found: C=68.61, H=5.78, N=6.14.

EXAMPLE 60

N-3-Methoxybenzyl-isophthalamic(4-hydroxymethyl-benzoic acid) ester

The title compound was synthesized in the same manner as Example 56. Microanalysis ($C_{24}H_{21}NO_6$): Calc'd: C=68.73, H=5.05, N=3.34. Found: C=68.93, H=4.85, N=3.30.

EXAMPLE 61

4-{[3-(3-Methoxy-benzylcarbamoyl)-benzoylamino]-methyl}-benzoic acid

The title compound was synthesized from Example 59 by hydrolysis of the methyl ester in the same manner as the second reaction in the synthesis of Example 55. Microanalysis ($C_{24}H_{22}N_2O_5$.0.40 $H_2O$): Calc'd: C=67.72, H=5.40, N=6.58. Found: C=67.68, H=5.34, N=6.41.

EXAMPLE 62

N-(3-Amino-benzyl)-N'-(3-methoxy-benzyl)-isophthalamide

The title compound was synthesized in the same manner as Example 19. Microanalysis ($C_{23}H_{23}N_3O_3$.0.30 $H_2O$): Calc'd: C=69.96, H=6.02, N=10.64. Found: C=69.96, H=6.04, N=10.39.

EXAMPLE 63

N-(3-Methoxy-benzyl)-N'-(3-nitro-benzyl)-isophthalamide

The title compound was synthesized in the same manner as Example 19. Microanalysis ($C_{23}H_{21}N_3O_5$.0.12 $H_2O$): Calc'd: C=65.52, H=5.08, N=9.97. Found: C=65.82, H=5.07, N=9.78.

EXAMPLE 64

4-Ethoxy-N'1, N"3-bis-(3-methoxy-benzyl)-isophthalamide

Into a flask was placed 4-hydroxy-isophthalic acid (25.46 g) and 200 mL of methanol. Concentrated sulfuric acid (20 mL) was slowly added. The mixture was refluxed for 48 hours; upon cooling a copious white precipitate formed, which was collected by filtration. The white solid obtained was washed with water, then dried under vacuum at 50° C. to yield 26.65 g of 4-hydroxy-isophthalic acid dimethyl ester. Iodoethane (3.8 mL, 47.5 mmol) was combined with the ester (5.0 g, 23.8 mmol), powdered cesium carbonate (3.3 g, 23.9 mmol) and anhydrous N,N'-dimethylformamide (40 mL). The mixture was stirred at room temperature overnight. The mixture was concentrated to give a white solid, which was partitioned between ethyl acetate (100 mL) and water (100 mL). The organic phase was further washed with 20 mL of brine, then dried with magnesium sulfate. Concentration yielded a clear oil, which was crystallized by the addition of a small amount of hexanes. The white crystals were collected by filtration and dried under vacuum to yield 5.17 g of 4-ethoxy-isophthalic acid di-methyl ester. This ester (5.10 g, 21.4 mmol) was placed in a mixture of 50% w/w sodium hydroxide (8.73 g) and 50 mL of water. Enough dioxane, about 10 mL, was added to solubilize the solid. The mixture was refluxed until all starting material had been consumed, about 1 hour. The solution was cooled, then acidified with concentrated hydrochloric acid until the pH of the solution was 1. The white precipitate obtained was collected by filtration, rinsed with water, then dried under vacuum overnight to yield 4.49 g of 4-ethoxy-isophthalic acid. This acid (2.0 g, 9.5 mmol) was refluxed in 10 mL of neat thionyl chloride for 3 hours. The excess thionyl chloride was evaporated at reduced pressure to give a white solid, which was dissolved in anhydrous tetrahydrofuran ("THF"), and evaporated at reduced pressure. Half of the resulting material was combined with 3-methoxy-benzylamine (1.22 mL, 9.5 mmol) triethylamine (2.0 mL, 14.3 mmol) and anhydrous THF (20 mL). The mixture was stirred until all the starting material was consumed, about 3 hours. The THF was evaporated at reduced pressure, and the white residue was dissolved in ethyl acetate (100 mL). The organic phase was washed with water (20 mL), 0.1N hydrochloric acid (20 mL), water (20 mL), and brine (20 mL). The organic phase was dried with magnesium sulfate and concentrated to give a white solid. The solid was recrystallized from hot ethyl acetate and collected by filtration. The solid was dried under vacuum at 40° C. to yield 1.56 g of the title compound. MS: M+1=449.2. Microanalysis ($C_{26}H_{28}N_2O_5$): Calc'd: C=69.63, H=6.29, N=6.25. Found: C=69.60, H=6.30, N=6.16.

EXAMPLE 65

N1,N3-Bis-1,3-benzodioxol-5-ylmethyl-4-ethoxy-isophthalamide

The title compound was prepared analogously to Example 64. MS: M+1=477.1. Microanalysis ($C_{26}H_{24}N_2O_7$): Calc'd: C=65.54, H=5.08, N=5.88. Found: C=65.32, H=5.16, N=5.79.

EXAMPLE 66

N1,N3-Bis-1,3-benzodioxol-5-ylmethyl-4-propoxy-isophthalamide

The title compound was prepared analogously to Example 64. MS: M+1=491.1. Microanalysis ($C_{27}H_{26}N_2O_7$): Calc'd: C=66.11, H=5.34, N=5.71. Found: C=65.90, H=5.30, N=5.65.

EXAMPLE 67

N1,N3-Bis-1,3-benzodioxol-5-ylmethyl-4-isopropoxy-isophthalamide

The title compound was prepared analogously to Example 64. MS: M+1=491.2. Microanalysis ($C_{27}H_{26}N_2O_7 \cdot 0.46 H_2O$): Calc'd: C=65.02, H=5.44, N=5.62. Found: C=65.02, H=5.46, N=5.80.

EXAMPLE 68

N1,N3-Bis-2,1,3-benzothiadiazol-5-ylmethyl-4-methoxy-isophthalamide

The title compound was synthesized in the same manner as Example 19. MS: M+1=491.1. Microanalysis ($C_{23}H_{18}N_6O_3S_2 \cdot 0.16 H_2O$): Calc'd: C=55.98, H=3.74, N=17.03. Found: C=55.98, H=3.70, N=16.71.

EXAMPLE 69

4-Methoxy-isophthalic acid di-2,1,3-benzothiadiazol-5-ylmethyl ester

The title compound was synthesized in the same manner as Example 3. MS: M+1=493.0. Microanalysis ($C_{23}H_{16}N_{34}O_5S_2 \cdot 1.18 H_2O$): Calc'd: C=53.77, H=3.60, N=10.90. Found: C=53.42, H=3.20, N=10.91.

The invention compounds of Formula I have been evaluated in standard assays for their ability to inhibit the activity of various MMP enzymes. The assays used to evaluate the biological activity of the invention compounds are well-known and routinely used by those skilled in the study of MMP inhibitors and their use to treat clinical conditions.

The assays measure the amount by which a test compound reduces the hydrolysis of a thiopeptolide substrate caused by a matrix metalloproteinase enzyme. Such assays are described in detail by Ye et al., in *Biochemistry*, 1992;31 (45):11231–11235, which is incorporated herein by reference.

Thiopeptolide substrates show virtually no decomposition or hydrolysis in the absence of a matrix metalloproteinase enzyme. A typical thiopeptolide substrate commonly utilized for assays is Ac-Pro-Leu-Gly-thioester-Leu-Leu-Gly-OEt. A 100-μL assay mixture will contain 50 mM of N-2-hydroxyethylpiperazine-N'-2-ethanesulfonic acid ("HEPES," pH 7.0), 10 mM $CaCl_2$, 100 μM thiopeptolide substrate, and 1 mM 5,5'-dithio-bis-(2-nitro-benzoic acid) (DTNB). The thiopeptolide substrate concentration is varied from 10 to 800 μM to obtain Km and Kcat values. The change in absorbance at 405 nm is monitored on a Thermo Max microplate reader (Molecular Devices, Menlo Park, Calif.) at room temperature (22° C.). The calculation of the amount of hydrolysis of the thiopeptolide substrate is based on $E_{412}=13600 M^{-1} cm^{-1}$ for the DTNB-derived product 3-carboxy-4-nitrothiophenoxide. Assays are carried out with and without matrix metalloproteinase inhibitor compounds, and the amount of hydrolysis is compared for a determination of inhibitory activity of the test compounds.

Several representative compounds have been evaluated for their ability to inhibit various matrix metalloproteinase enzymes. Table 1 below presents inhibitory activity for compounds from various classes. In the table, MMP-1FL refers to full length interstitial collagenase; MMP-3CD refers to the catalytic domain of stromelysin-1; MMP-13CD refers to the catalytic domain of collagenase-3. Test compounds were evaluated at various concentrations in order to determine their respective $IC_{50}$ values, the nanomolar ("nM") concentration of compound required to cause a 50% inhibition of the hydrolytic activity of the respective enzyme.

It should be appreciated that the assay buffer used with MMP-3CD was 50 mM N-morpholinoethanesulfonate ("MES") at pH 6.0 rather than the HEPES buffert at pH 7.0 described above.

TABLE 1

| Example No. | MMP-1FL $IC_{50}$ (nM) | MMP-3CD $IC_{50}$ (nM) | MMP-13CD $IC_{50}$ (nM) |
|---|---|---|---|
| 1 | >100,000 | 82,000 | 250 |
| 2 | nt | nt | 1100 |
| 3 | >100,000 | >30,000 | 1167 |
| 4 | >100,000 | >100,000 | 900 |
| 5 | >100,000 | >100,000 | 255 |
| 6 | nt | nt | 1500 |
| 7 | >100,000 | 73,000 | 1100 |
| 8 | >100,000 | >100,000 | 2333 |
| 9 | >100,000 | >30,000 | 2300 |
| 10 | 79,000 | 9400 | 5500 |
| 11 | >100,0040 | >30,000 | 7833 |
| 12 | >100,000 | 51,000 | 1075 |
| 13 | >100,000 | >100,000 | 1150 |
| 14 | nt | nt | 660 |
| 15 | >100,000 | >100,000 | 2350 |
| 16 | >100,000 | >30,000 | 1000 |
| 17 | >100,000 | >100,000 | 5650 |
| 18 | >100,000 | 20,000 | 2300 |
| 19 | >100,000 | 69,000 | 330 |
| 20 | >100,000 | >100,000 | 8200 |
| 21 | >100,000 | >100,000 | 9250 |
| 22 | >100,000 | 50,000 | 185 |
| 23 | nt | nt | 200 |
| 24 | >100,000 | >100,000 | 280 |
| 25 | nt | nt | 400 |
| 26 | nt | nt | 430 |
| 27 | nt | nt | 810 |
| 28 | >100,000 | 81,000 | 683 |
| 29 | nt | nt | 1500 |
| 30 | >100,000 | >100,000 | 1350 |
| 31 | >100,000 | >100,000 | 1900 |
| 32 | >100,000 | >100,000 | 1650 |

TABLE 1-continued

| Example No. | MMP-1FL IC$_{50}$ (nM) | MMP-3CD IC$_{50}$ (nM) | MMP-13CD IC$_{50}$ (nM) |
|---|---|---|---|
| 33 | >100,000 | >100,000 | 1800 |
| 34 | >100,000 | >100,000 | 2425 |
| 35 | nt | nt | 3100 |
| 36 | nt | nt | 4400 |
| 37 | >100,000 | >100,000 | 3400 |
| 38 | nt | nt | 5700 |
| 39 | >100,000 | >100,000 | 2740 |
| 40 | >100,000 | nt | 7800 |
| 41 | nt | nt | 8700 |
| 42 | >100,000 | >100,000 | 7250 |
| 43 | >100,000 | >100,000 | 180 |
| 44 | nt | nt | 190 |
| 45 | nt | nt | 4100 |
| 46 | nt | nt | 5200 |
| 47 | >100,000 | >100,000 | 7930 |
| 48 | >100,000 | >100,000 | 1400 |
| 49 | >100,000 | >100,000 | 1500 |
| 50 | >100,000 | >100,000 | 503 |
| 51 | >100,000 | 68,000 | 555 |
| 52 | >100,000 | 40,000 | 415 |
| 53 | >100,000 | 76,000 | 385 |
| 54 | >100,000 | >100,000 | 930 |
| 55 | >100,000 | >100,000 | 915 |
| 56 | >100,000 | 30,000 | 33 |
| 57 | nt | nt | 2500 |
| 58 | >100,000 | >100,000 | 1135 |
| 59 | >100,000 | 64,000 | 255 |
| 60 | >100,000 | >100,000 | 44 |
| 61 | >100,000 | >100,000 | 77 |
| 62 | >100,000 | >100,000 | 935 |
| 63 | nt | nt | 2100 |
| 64 | >100,000 | >100,000 | 1833 |
| 65 | 51,000 | 20,000 | 493 |
| 66 | >100,000 | 27,000 | 1450 |
| 67 | 71,000 | 30,000 | 3750 |
| 68 | 30,000 | 21,000 | 155 |
| 69 | 30,000 | 30,000 | 370 | nt = Not tested.

The foregoing data establish that the invention compounds of Formula I are potent inhibitors of MMP enzymes and are especially useful due to their selective inhibition of MMP-13. Because of this potent and selective inhibitory activity, the invention compounds are especially useful to treat diseases mediated by the MMP enzymes, and particularly those mediated by MMP-13.

Administration of a compound of Formula I, or a pharmaceutically acceptable salt thereof, to a mammal to treat the diseases mediated by MMP enzymes is preferably, although not necessarily, accomplished by administering the compound, or the salt thereof, in a pharmaceutical dosage form.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 to 1000 mg, preferably 10 to 100 mg according to the particular application and the potency of the active component. The composition can, if desired, also contain other compatible therapeutic agents.

In therapeutic use as agents to inhibit a matrix metalloproteinase enzyme for the treatment of atherosclerotic plaque rupture, aortic aneurism, heart failure, restenosis, periodontal disease, corneal ulceration, cancer metastasis, tumor angiogenesis, arthritis, or other autoimmune or inflammatory disorders dependent upon breakdown of connective tissue, the compounds utilized in the pharmaceutical method of this invention are administered at a dose that is effective to inhibit the hydrolytic activity of one or more matrix metalloproteinase enzymes. The initial dosage of about 1 mg/kg to about 100 mg/kg daily will be effective. A daily dose range of about 25 mg/kg to about 75 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired. Typical dosages will be from about 0.1 mg/kg to about 500 mg/kg, and ideally about 25 mg/kg to about 250 mg/kg, such that it will be an amount which is effective to treat the particular disease being prevented or controlled.

The following examples illustrate typical formulations provided by the invention.

FORMULATION EXAMPLE 1

| Tablet Formulation | |
| --- | --- |
| Ingredient | Amount (mg) |
| Compound of Example 56 | 25 |
| Lactose | 50 |
| Cornstarch (for mix) | 10 |
| Cornstarch (paste) | 10 |
| Magnesium stearate (1%) | 5 |
| Total | 100 |

The isophthalic amide of Example 56, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of atherosclerosis or arthritis.

FORMULATION EXAMPLE 2

| Preparation for Oral Solution | |
| --- | --- |
| Ingredient | Amount |
| Compound of Example 4 | 400 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the isophthalic ester of Example 4 is dissolved therein. The saccharin, sodium benzoate, flavor, and dye are added and dissolved. The volume is adjusted to 100 mL with distilled water. Each milliliter of syrup contains 4 mg of invention compound.

FORMULATION EXAMPLE 3

Parenteral Solution

In a solution of 700 mL of propylene glycol and 200 mL of water for injection is suspended 20 g of the compound of Example 30. After suspension is complete, the pH is adjusted to 6.5 with 1N sodium hydroxide, and the volume is made up to 1000 mL with water for injection. The formulation is sterilized, filled into 5.0-mL ampoules each containing 2.0 mL, and sealed under nitrogen.

As matrix metalloproteinase inhibitors, the compounds of Formula I are useful as agents for the treatment of multiple sclerosis. They are also useful as agents for the treatment of atherosclerotic plaque rupture, restenosis, periodontal disease, corneal ulceration, treatment of burns, decubital ulcers, wound repair, heart failure, cancer metastasis, tumor angiogenesis, arthritis, and other inflammatory disorders dependent upon tissue invasion by leukocytes.

It should be appreciated that in all invention embodiments described above or in the claims below, whenever an R group such as, for example, $R^1$, $R^2$, $R^3$, $R^4$, $R^5$, $R^6$, $R^7$, $R^8$, or $R^9$, is used more than once to define an invention compound, each use of the R group is independent of any other use of that same R group or, for that matter, any other R group, unless otherwise specified.

What is claimed is:

1. A method for treating rheumatoid arthritis, osteoarthritis, or congestive heart failure, the method comprising administering to a patient suffering from rheumatoid arthritis, osteoarthritis, or heart failure a therapeutically effective amount of a compound of Formula III

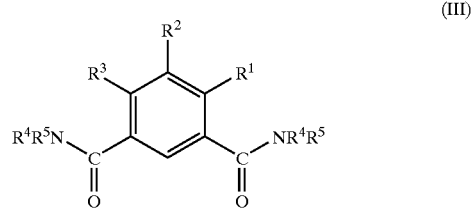

(III)

wherein:
R¹, R², and R³ independently are hydrogen, halo, hydroxy, $C_1$–$C_6$ alkyl, $C_1$–$C_6$ alkoxy, $C_2$–$C_6$ alkenyl, $C_2$–$C_6$ alkynyl, $NO_2$, $NR^4R^5$, CN, or $CF_3$;

R⁴ and R⁵ independently are $(CH_2)_n$ heterocyclyl, $(CH_2)_n$ heteroaryl, or R⁴ and R⁵ when taken together with the nitrogen to which they are attached complete a 3- to 8-membered ring, optionally having a heteroatom selected from O, S, or NH, and optionally substituted or unsubstituted;

n is an integer from 0 to 6;

or a pharmaceutically acceptable salt thereof.

2. A method for treating rheumatoid arthritis, osteoarthritis, or congestive heart failure, the method comprising administering to a patient suffering from rheumatoid arthritis, osteoarthritis, or heart failure a therapeutically effective amount of a compound of Formula VI

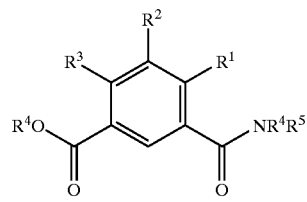

or a pharmaceutically acceptable salt thereof,
wherein:
R¹, R², and R³ independently are hydrogen, halo, hydroxy, $C_1$–$C_6$ alkyl, $C_1$–$C_6$ alkoxy, $C_2$–$C_6$ alkenyl, $C_2$–$C_6$ alkynyl, $NO_2$, $NR^4R^5$, CN, or $CF_3$;

R⁴ and R⁵ independently are $(CH_2)_n$ heterocyclyl, $(CH_2)_n$ heteroaryl, or R⁴ and R⁵ when taken together with the nitrogen to which they are attached complete a 3- to 8-membered ring, optionally having a heteroatom selected from O, S, or NH, and optionally substituted or unsubstituted; and n is an integer from 0 to 6.

3. A compound selected from the group consisting of:
Isophthalic acid di-(2,1,3-benzothiadiazol-5-yl) methyl ester;
4-Methoxy-isophthalic acid dipyridin-4-ylmethyl ester;
N,N'-Bis-1,3-benzodioxol-5-ylmethyl-4-methoxy-isophthalamide;
N-1,3-Benzodioxol-5-yhmethyl-N'-furan-2-ylmethyl-isophthalamide;
4-Methoxy-isophthalic acid di-2,1,3-benzothiadiazol-5-ylmethyl ester;
N1,N3-Bis-1,3-benzodioxol-5-ylmethyl-4-ethoxy-isophthalamide;
N1-1,3-Benzodioxol-5-ylmethyl-N3-pyridin-3-ylmethyl-isophthalamide;
N1,N3-Bis-1,3-benzodioxol-5-ylmethyl-4-isopropoxy-isophthalamide;
4-Amino-N1,N3-bis-1,3-benzodioxol-5-ylmethyl-isophthalamide;
4-Acetylamino-N1,N3-bis-1,3-benzodioxol-5-ylmethyl-isophthalamide;
N1-1,3-Benzodioxol-5-ylmethyl-N3-pyridin-3-ylmethyl-isophthalamide;
N1,N3-Bis-1,3-benzodioxol-5-ylmethyl-4-propoxy-isophthalamide; and
N1,N3-Bis-2,1,3-benzothiadiazol-5-yhmethyl-4-methoxy-isophthalamide.

4. A compound of Formula III

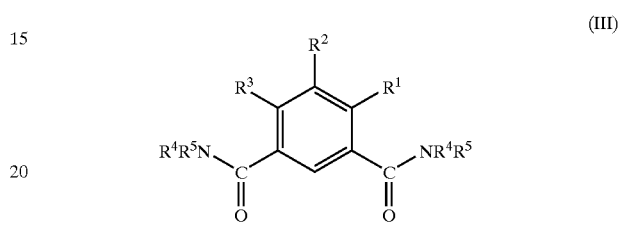

wherein:
R¹, R², and R³ independently are hydrogen, halo, hydroxy, $C_1$–$C_6$ alkyl, $C_1$–$C_6$ alkoxy, $C_2$–$C_6$ alkenyl, $C_2$–$C_6$ alkynyl, $NO_2$, $NR^4R^5$, CN, or $CF_3$;

R⁴ and R⁵ independently are $(CH_2)_n$ heterocyclyl, $(CH_2)_n$ heteroaryl, or R⁴ and R⁵ when taken together with the nitrogen to which they are attached complete a 3- to 8-membered ring, optionally having a heteroatom selected from O, S, or NH, and optionally substituted or unsubstituted;

n is an integer from 0 to 6;

or a pharmaceutically acceptable salt thereof.

5. A pharmaceutical composition, comprising a compound of claim 4, or a pharmaceutically acceptable salt thereof, admixed with a pharmaceutically acceptable carrier, diluent, or excipient.

6. A method for treating rheumatoid arthritis, the method comprising administering to a patient suffering from rheumatoid arthritis a therapeutically effective amount of a compound of claim 4, or a pharmaceutically acceptable salt thereof.

7. A method for treating osteoarthritis, the method comprising administering to a patient suffering from osteoarthritis a therapeutically effective amount of a compound of claim 4, or a pharmaceutically acceptable salt thereof.

8. A method for treating congestive heartfailure, the method comprising administering to a patient suffering from heart failure a therapeutically effective amount of a compound of claim 4, or a pharmaceutically acceptable salt thereof.

* * * * *